US009826967B2

(12) United States Patent
Druma et al.

(10) Patent No.: US 9,826,967 B2
(45) Date of Patent: *Nov. 28, 2017

(54) CANNULA AND METHODS OF USE

(71) Applicant: Kyphon SARL, Neuchatel (CH)

(72) Inventors: Calin Druma, San Jose, CA (US); Craig E. Lauchner, Sunnyvale, CA (US)

(73) Assignee: Kyphon SÀRL, Neuchâtel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/619,547

(22) Filed: Feb. 11, 2015

(65) Prior Publication Data

US 2015/0366583 A1     Dec. 24, 2015

Related U.S. Application Data

(62) Division of application No. 14/309,604, filed on Jun. 19, 2014, now Pat. No. 9,675,333.

(51) Int. Cl.
| | |
|---|---|
| *A61B 17/34* | (2006.01) |
| *A61B 17/02* | (2006.01) |
| *A61B 90/30* | (2016.01) |
| *A61B 17/00* | (2006.01) |
| *A61B 17/70* | (2006.01) |

(52) U.S. Cl.
CPC ...... *A61B 17/0218* (2013.01); *A61B 17/0293* (2013.01); *A61B 17/3421* (2013.01); *A61B 17/3423* (2013.01); *A61B 90/30* (2016.02); *A61B 17/3439* (2013.01); *A61B 17/7074* (2013.01); *A61B 2017/00477* (2013.01); *A61B 2017/00951* (2013.01); *A61B 2017/00991* (2013.01); *A61B 2017/346* (2013.01); *A61B 2017/3407* (2013.01); *A61B 2017/3433* (2013.01); *A61B 2017/3458* (2013.01); *A61B 2017/3492* (2013.01); *A61B 2090/309* (2016.02)

(58) Field of Classification Search
CPC ............ A61B 17/3415; A61B 17/3417; A61B 17/3421; A61B 17/3423; A61B 17/3431; A61B 17/3439; A61B 2017/3422; A61B 8/4236; A61M 25/0023; A61M 29/00; A61M 2025/0024
See application file for complete search history.

(56) References Cited

U.S. PATENT DOCUMENTS

| | | | |
|---|---|---|---|
| 2,697,433 A | 12/1954 | Zehnder | |
| 3,788,318 A * | 1/1974 | Kim | ................. A61M 5/00 604/104 |
| 3,789,852 A * | 2/1974 | Kim | ................. A61B 17/3439 604/104 |
| 4,608,977 A | 9/1986 | Brown | |
| 5,201,742 A | 4/1993 | Hasson | |
| 5,540,675 A | 7/1996 | Hasson | |
| 5,772,654 A | 6/1998 | Leyva | |
| 5,785,648 A * | 7/1998 | Min | ................. A61B 1/32 600/206 |

(Continued)

*Primary Examiner* — Anu Ramana

(57) ABSTRACT

A surgical instrument comprises a handling portion with a control junction and a plurality of vertical members operatively disposed within the control junction. The handling portion includes a top nut. Manipulation of the handling portion allows the vertical members to toggle between a narrowed configuration and an expanded configuration. Systems and methods are disclosed.

20 Claims, 23 Drawing Sheets

(56) References Cited

U.S. PATENT DOCUMENTS

| | | | |
|---|---|---|---|
| 6,436,119 B1* | 8/2002 | Erb | A61B 17/3417 |
| | | | 606/185 |
| 7,374,534 B2* | 5/2008 | Dalton | A61B 17/0218 |
| | | | 600/222 |
| 8,282,546 B2* | 10/2012 | Shelton, IV | A61B 1/32 |
| | | | 600/206 |
| 8,308,740 B2 | 11/2012 | Tolley et al. | |
| 8,361,091 B2 | 1/2013 | Schein et al. | |
| 8,460,187 B2* | 6/2013 | Bouquet | A61M 29/00 |
| | | | 600/222 |
| 8,500,759 B2 | 8/2013 | Koyfman et al. | |
| 8,603,078 B2 | 12/2013 | Stefanchik et al. | |
| 2001/0012950 A1* | 8/2001 | Nishtala | A61M 25/0662 |
| | | | 606/198 |
| 2006/0224044 A1 | 10/2006 | Marchek et al. | |
| 2007/0060939 A1* | 3/2007 | Lancial | A61B 1/00154 |
| | | | 606/191 |
| 2007/0100210 A1* | 5/2007 | Selover | A61B 17/3423 |
| | | | 600/199 |
| 2009/0326462 A1 | 12/2009 | Wingardner, III et al. | |
| 2011/0144589 A1* | 6/2011 | Ortiz | A61B 17/3423 |
| | | | 604/164.03 |
| 2012/0220918 A1* | 8/2012 | Chaffringeon | A61F 13/266 |
| | | | 604/11 |

\* cited by examiner

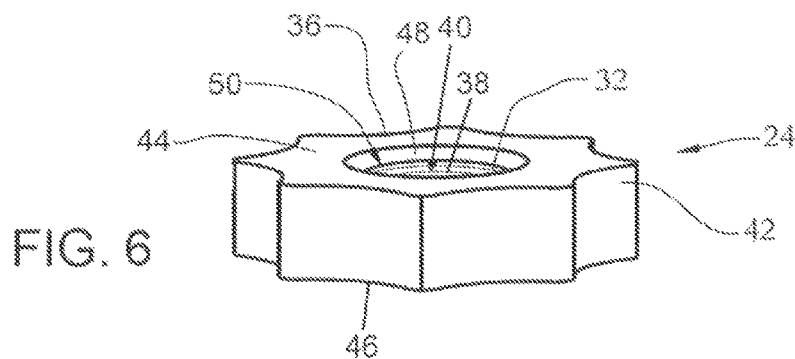
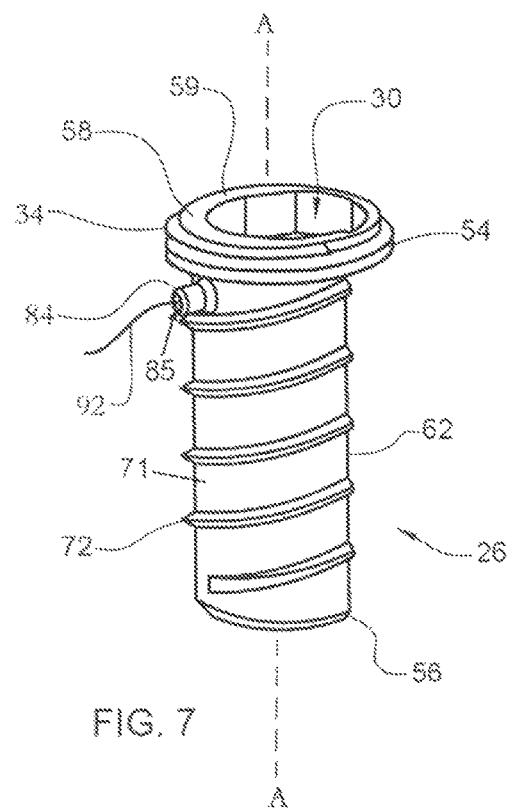
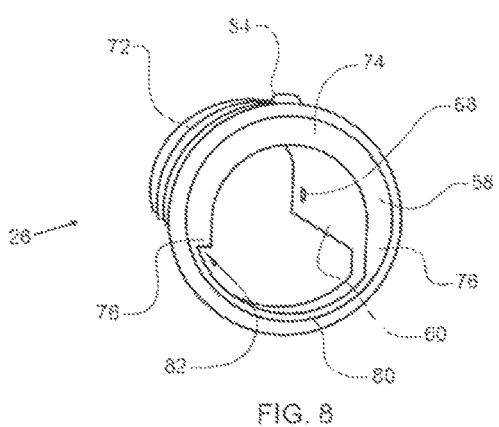

CANNULA AND METHODS OF USE

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders comprises fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

During certain decompression procedures, patients may be conscious and, as a result, these patients can move, forcing their back muscles to contract. Such contractions can push cannulas dorsally, which can cause bleeding in the working zone and a need to push the cannula ventrally. As surgeons manipulate cannulas, a hand is used to wag and hold the cannula top. However, the cannula may slip out of the position set by the surgeon. A cannula is needed to prevent such movement of the cannula.

SUMMARY

In one embodiment, a surgical instrument is provided. The surgical instrument comprises a handling portion with a control junction. The handling portion can comprise a top nut. The surgical instrument also comprises a plurality of vertical members, the proximal ends of which are disposed within the control junction. Manipulation of the handling portion allows the vertical members to toggle between a narrowed configuration and an expanded configuration. The control junction can also be at least partially housed or completely housed by a gripping portion such that threads on the gripping portion engage threads on the top nut to allow the top nut to be axially translatable relative to the holding member upon rotation of the top nut relative to the gripping portion. In one embodiment, the control junction can be at least partially housed or completely housed by the holding member in a telescopic relationship to the top nut and wherein the top nut is movable relative to the holding member. In another embodiment, the control junction is bordered by an end surface of the top nut.

In another embodiment, a first vertical member extends along a first longitudinal axis between a proximal end and a distal end of the first vertical member. The first vertical member comprises an inner surface that defines a passageway and a flange at the proximal end of the first vertical member. A second vertical member extends along a second longitudinal axis between a proximal end and a distal end of the second vertical member. The proximal end of the second vertical member comprises a lip that extends at an acute angle relative to the second longitudinal axis. The distal end of the second vertical member is movably positioned in the passageway. The surgical instrument can be movable between a narrowed configuration in which the second longitudinal axis is parallel to the first longitudinal axis and an expanded configuration in which the second longitudinal axis is at an acute angle relative to the first longitudinal axis. In another embodiment, the proximal end of one of the vertical members is configured to contact the end surface when the vertical members are in the expanded configuration.

In one embodiment, a method of performing a surgical procedure with the surgical instrument described herein is provided. The method comprises positioning the surgical instrument such that the vertical members are in the narrowed configuration and rotating the top nut such that proximal ends of the vertical members move within the control junction to move the vertical members from the narrowed configuration to the expanded configuration. The method can further comprise adjusting the position of the surgical instrument after rotation of the top nut using the holding member.

BRIEF DESCRIPTION OF THE DRAWINGS

The present disclosure will become more readily apparent from the specific description accompanied by the following drawings, in which:

FIG. 6 is a perspective view of a component of the system shown in FIG. 1;

FIG. 7 is a perspective view of a component of the system shown in FIG. 1;

FIG. 8 is a top, perspective view of a component of the system shown in FIG. 1;

DETAILED DESCRIPTION

Figure 1:
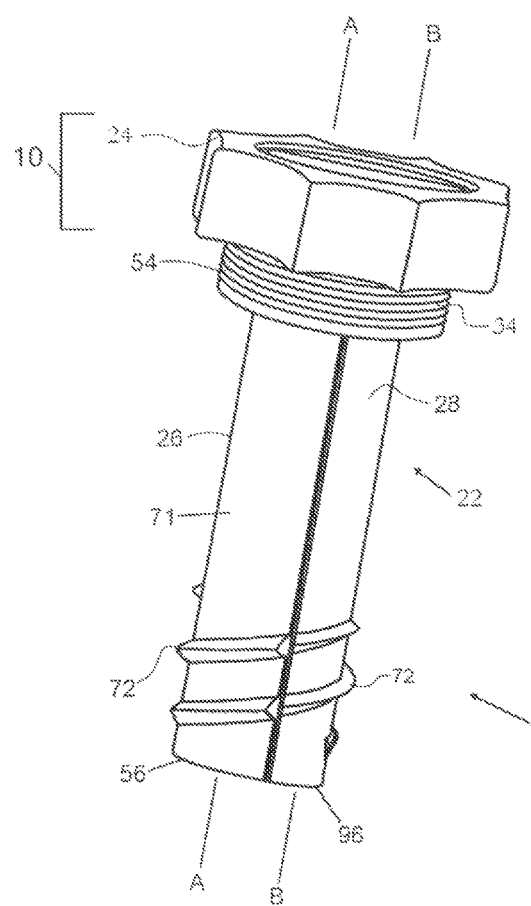
FIG. 1 is a perspective view of a surgical system, in accordance with the principles of the present disclosure.

The exemplary embodiments of a surgical system and related methods of use disclosed are discussed in terms of medical devices for the treatment of musculoskeletal disorders and more particularly, in terms of a surgical system and method for accessing a surgical site to facilitate treatment. In one embodiment, the surgical system comprises a surgical instrument, such as, for example, cannulas that reduce costs and provide unique features that address unmet needs. In some embodiments, the surgical instrument comprises one or a plurality of light sources for illuminating a patient's anatomy, thereby increasing visualization at the treatment site. In some embodiments, the surgical instrument comprises one or more integrated LEDs near a bottom or distal tip or on another portion of the surgical instrument for illuminating tissue without shadows, thereby increasing effective visualization. The surgical instruments described herein are configured for use by medical practitioners in connection with surgical procedures, such as, for example, decompression procedures. In some procedures in which the patient remains conscious, the surgical instrument is configured to remain stationary as a patient moves or muscles contract thus avoiding unintended movement of the surgical instrument and possible injury caused by such movement as discussed below.

In some embodiments, the surgical instrument comprises an expandable cannula. The instrument can be anchored to surrounding tissue by screwing the surgical instrument over a dilator, such as, for example, a last sequential dilator, to secure the surgical instrument in place in tissue, such as, for example, muscle. In some embodiments, the surgical instrument is retracted after the surgical instrument is screwed over the dilator, to further secure the surgical instrument. The surgical instrument can be circumferentially continuous, eliminating the need for time consuming bleeding control. This feature allows a medical practitioner to save a good deal of time by reducing the need for cauterizing tools. This feature also allows the medical practitioner to accurately limit the expanded size of the cannula. In some embodiments, the surgical instrument is made entirely from injection molded parts and may be disposable.

The surgical instruments of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. The surgical system of the present disclosure may be employed with other osteal and bone related applications, including those associated with diagnostics and therapeutics. The disclosed surgical system may be employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to this detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value comprises at least that particular value, unless the context clearly dictates otherwise. Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment comprises preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically comprises procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" comprises soft tissue, ligaments, tendons, cartilage and/or bone unless specifically referred to otherwise.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or comprise fastening elements and/or instruments, as described herein.

Figure 1A:
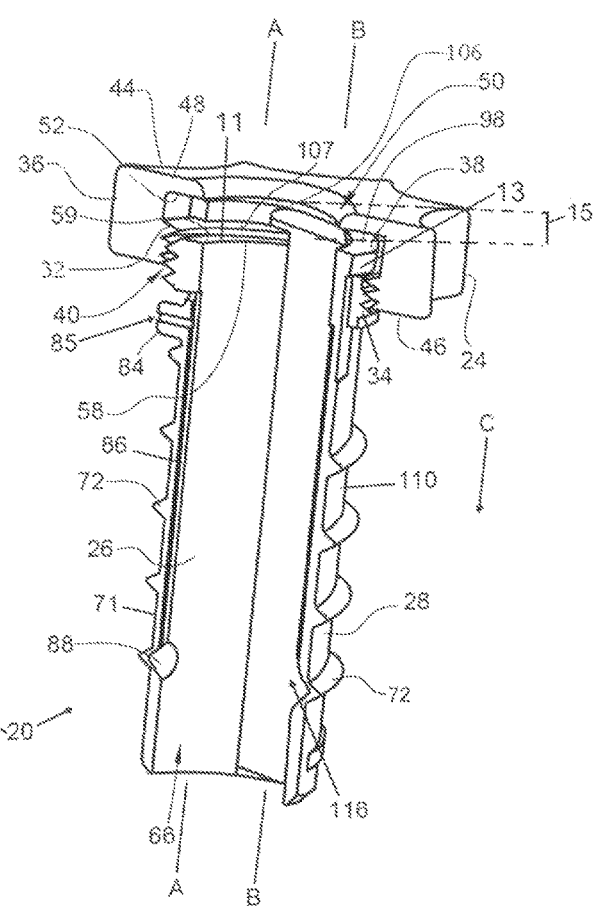
FIG. 1A is a cross-sectional view of components of the system shown in FIG. 1.
Figure 4:
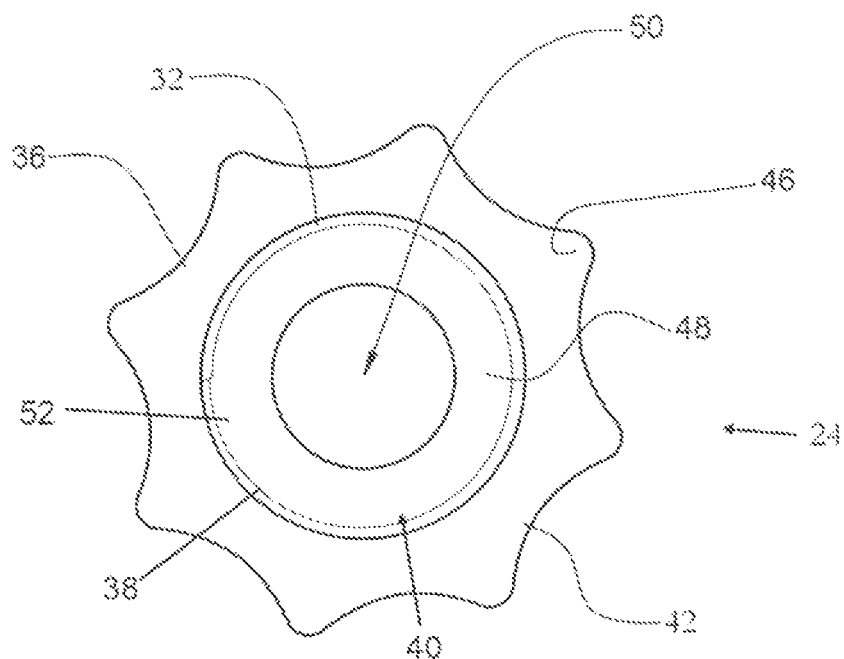
FIG. 4 is a bottom view of a component of the system shown in FIG. 1.
Figure 4A:
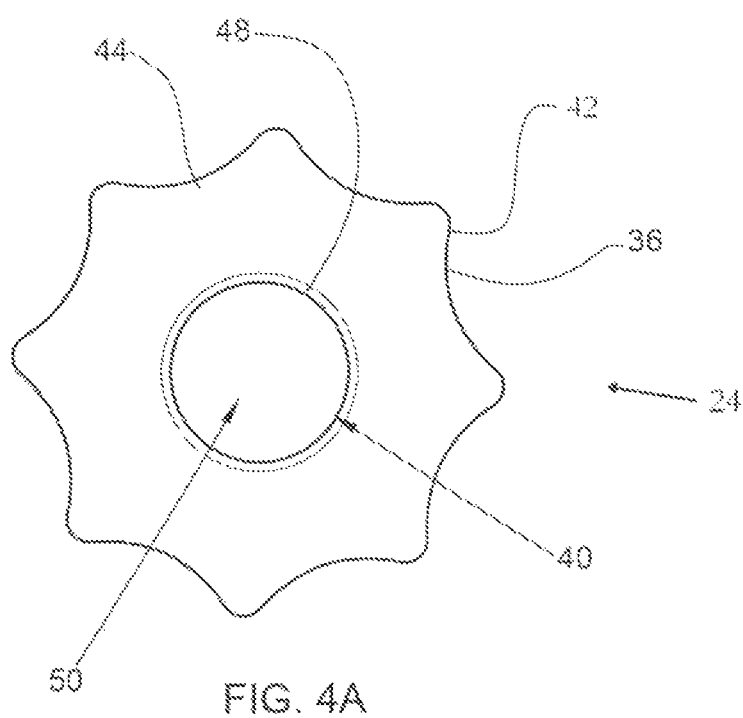
FIG. 4A is a top view of a component of the system shown in FIG. 1.

Cannula 22 comprises a handling portion 10, which comprises a top nut 24, and a plurality of vertical members 26 and 28. A first vertical member 26 and a second vertical member 28 are shown in FIGS. 1 and 1A, for example. Proximal ends 11, 13 of vertical members 26, 28 are disposed within the control junction 15 of the handling portion 10. A portion of the control junction 15 is defined by the end surface 52 of the top nut 24, as shown in FIG. 1A. An inner or internal thread 32 of top nut 24, shown in FIG. 4, is configured to engage an external thread 34 on proximal end 11 of vertical member 26.

Figure 2A:
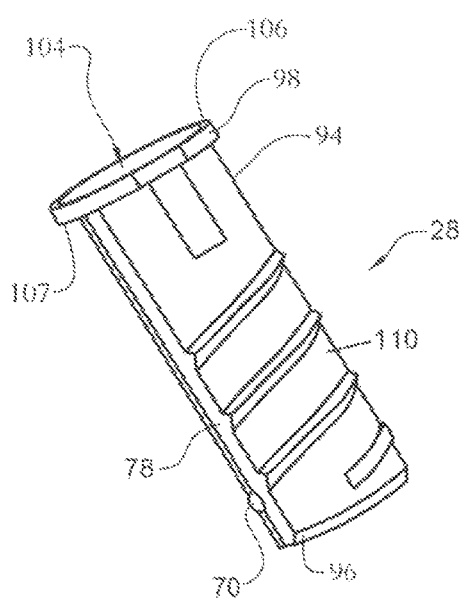
FIG. 2A is a perspective view of a component of the system shown in FIG. 1.
Figure 2B:
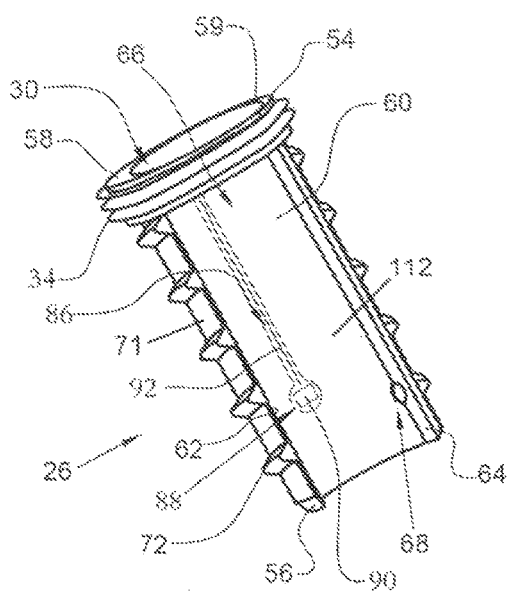
FIG. 2B is a perspective view of a component of the system shown in FIG. 1.
Figure 3:
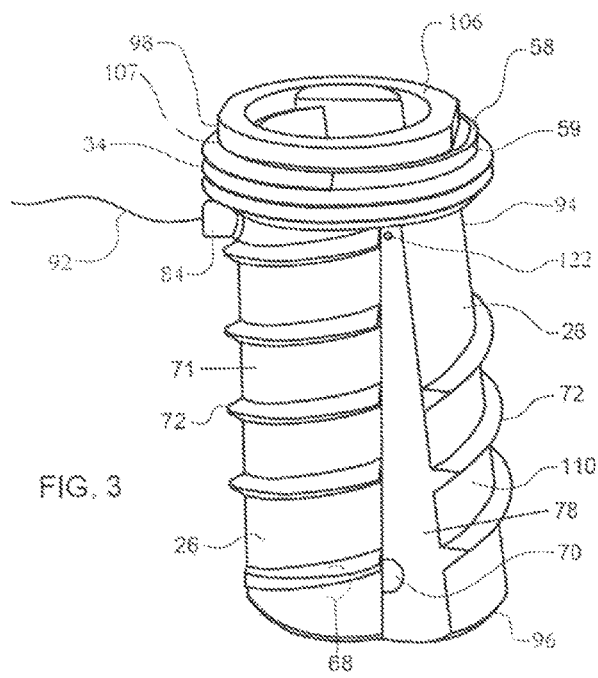
FIG. 3 is a perspective view of components of the system shown in FIG. 1.

Second vertical member 28, shown in FIG. 2A, is configured to be positioned through an opening 30 in first vertical member 26, shown in FIG. 2B, to produce the cannula 22 shown in FIG. 3. The outer or external thread 34 of first vertical member 26 contacts the internal thread 32 of top nut 24, all within the control junction 15.

Figure 5:
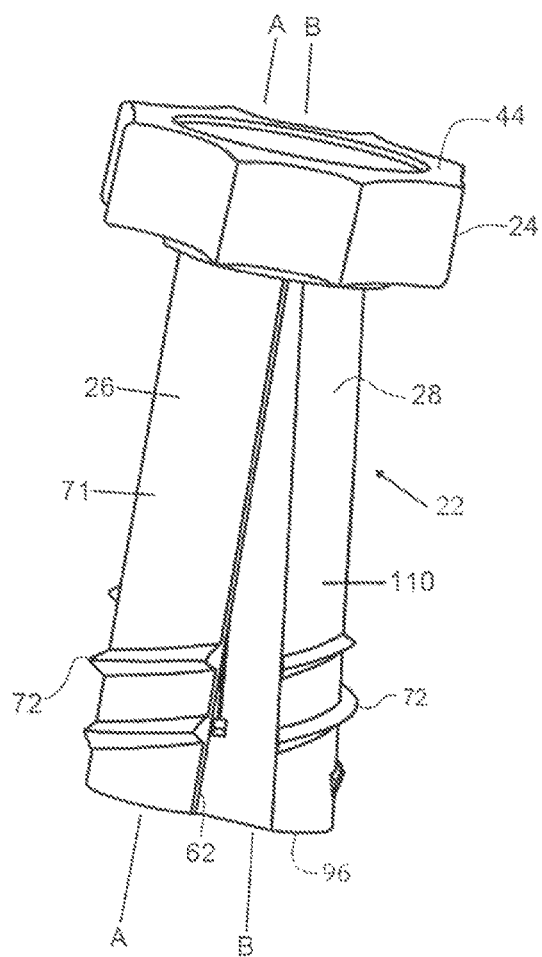
FIG. 5 is a perspective view of components of the system shown in FIG. 1.

The handling portion 10, which comprises top nut 24, may be manipulated to allow the vertical members 26, 28 to toggle between a narrowed configuration and an expanded configuration. For example, top nut 24 can be rotated relative to first vertical member 26 such that cannula 22 moves from the narrowed configuration shown in FIGS. 1 and 1A to the expanded configuration shown in FIGS. 5 and 5A. When cannula 22 is in the narrowed configuration, second vertical member 28 extends parallel to first vertical member 26 and when cannula 22 is in the expanded configuration, second vertical member 28 extends transverse to first vertical member 26.

Top nut 24 comprises a body 36 including an inner surface 38 defining a throughhole 40, and having an inner thread 32 as shown in FIG. 6, for example. Throughhole 40 may have a cylindrical or polygonal cross sectional configuration and inner thread 32 may have different pitches. The top nut 24 may also comprise a gripping portion 42 configured for gripping by a medical practitioner.

Figure 5A:
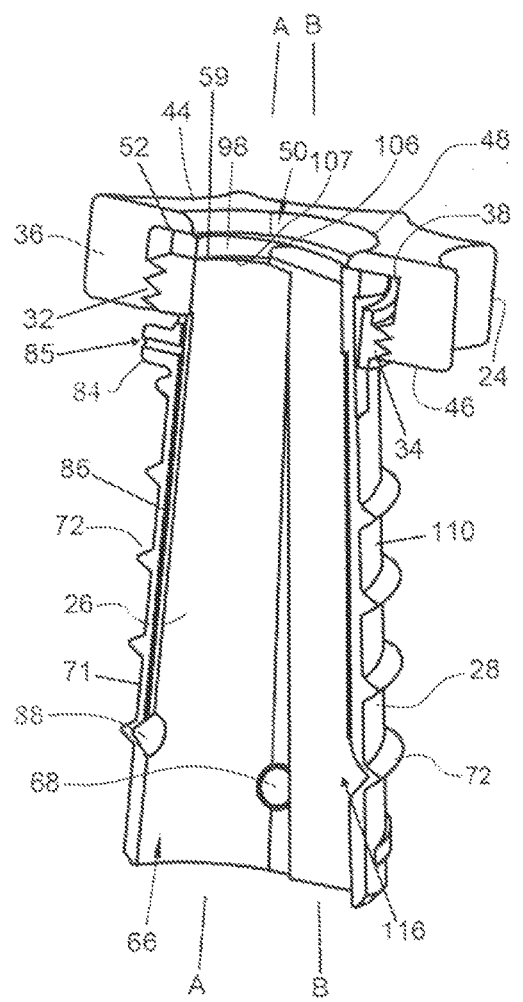
FIG. 5A is a cross-sectional view of components of the system shown in FIG. 1.

Body 36 of top nut 24 extends between a first end 44 of body 36 and an opposite second end 46 of body 36. First end 44 comprises a projection 48 extending inwardly from body 36, as shown in FIGS. 1A, 4 and 5A, for example. Projection 48 defines a throughhole 50 extending through an upper surface of body 36. In some embodiments, throughhole 50 has a cylindrical cross sectional configuration and a diameter that is less than that of throughhole 40, as shown in FIG. 4, for example. Projection 48 comprises an end surface 52 opposite the upper surface of body 36. End surface 52 of top nut 24 can be planar and extend perpendicular to a longitudinal axis defined by body 36 of top nut 24. In some embodiments, end surface 52 may be disposed at alternate orientations relative to the longitudinal axis defined by body 36, such as, for example, transverse, perpendicular and/or other angular orientations such as acute or obtuse, co-axial and/or may be offset or staggered. The second end 46 can further comprise an adhesive surface for contacting the skin of a patient.

First vertical member 26 extends along a longitudinal axis A between a first end 54 of first vertical member 26 and an opposite second end 56 of first vertical member 26. First end 54 of first vertical member 26 comprises a flange 58. In some embodiments, flange 58 extends perpendicular to axis A. Flange 58 of first vertical member 26 comprises an upper surface 59 that may be planar and extend perpendicular to longitudinal axis A. First vertical member 26 comprises an inner surface 60, as shown in FIG. 8, for example. In some embodiments, inner surface 60 is concavely curved between axial surfaces 62, 64 of first vertical member 26 and defines a passageway 66 of first vertical member 26, as shown in FIG. 2B, for example. In some embodiments, passageway 66 has a semi-circular cross sectional configuration. Flange 58 of first vertical member 26 defines opening 30 of first vertical member 26. That is, opening 30 of first vertical member 26 extends through flange 58 and is in communication with passageway 66 of first vertical member 26.

In some embodiments, inner surface 60 of first vertical member 26 comprises a recess 68 that is configured for disposal of a protrusion 70 of second vertical member 28 to provisionally fix second vertical member 28 relative to first vertical member 26, as will be discussed. In some embodiments, recess 68 of first vertical member 26 is concavely curved. In some embodiments, first vertical member 26 comprises a first recess 68 adjacent axial surface 62 of first vertical member 26 and a second recess 68 adjacent axial surface 64 of first vertical member 26. First vertical member 26 may comprises one or a plurality of recesses 68.

Figure 9:
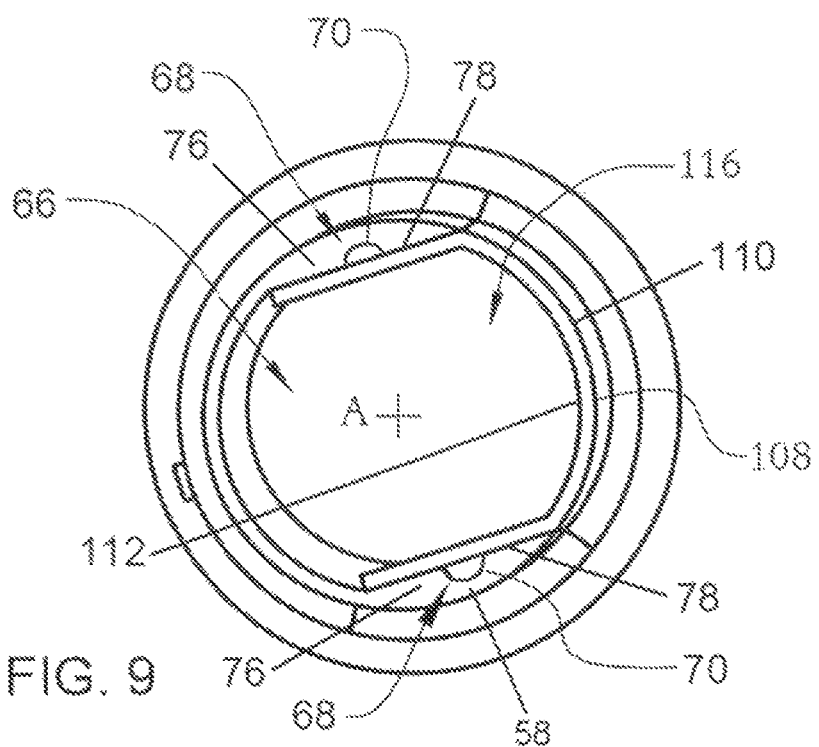
FIG. 9 is a bottom view of components of the system shown in FIG. 1.
Figure 10:
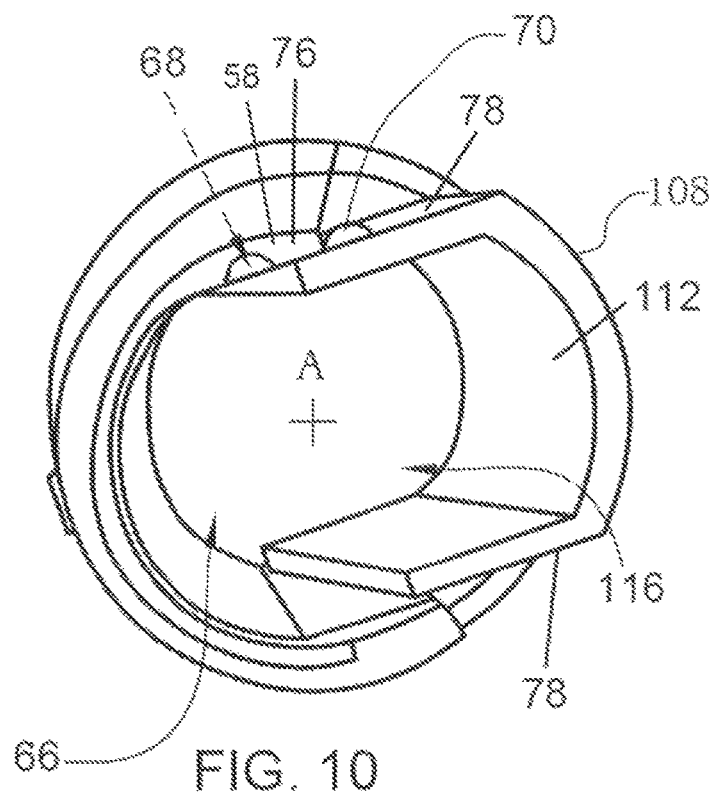
FIG. 10 is a bottom view of components of the system shown in FIG. 1.

In some embodiments, flange 58 of first vertical member 26 comprises an arcuate portion 74 extending between planar or linear portions 76 of flange 58, as shown in FIG. 8, for example. Arcuate portion 74 of flange 58 may be concave and may be continuously curved between linear portions 76 of flange 58. In some embodiments, linear portions 76 of flange 58 extend parallel to one another and are configured to engage planar side walls 78 of second vertical member 28, as shown in FIGS. 9 and 10, for example. In some embodiments, flange 58 comprises a second arcuate portion 80 opposite arcuate portion 74, as shown in FIG. 8, for example. Second arcuate portion 80 may be concave and continuously curved. In some embodiments, flange 58 comprises an indent 82 at an interface between second arcuate portion 80 of flange 58 and one of linear portions 76 of flange 58, as shown in FIG. 8, for example. Indent 82 of flange 58 facilitates assembly of cannula 22.

Figure 11:
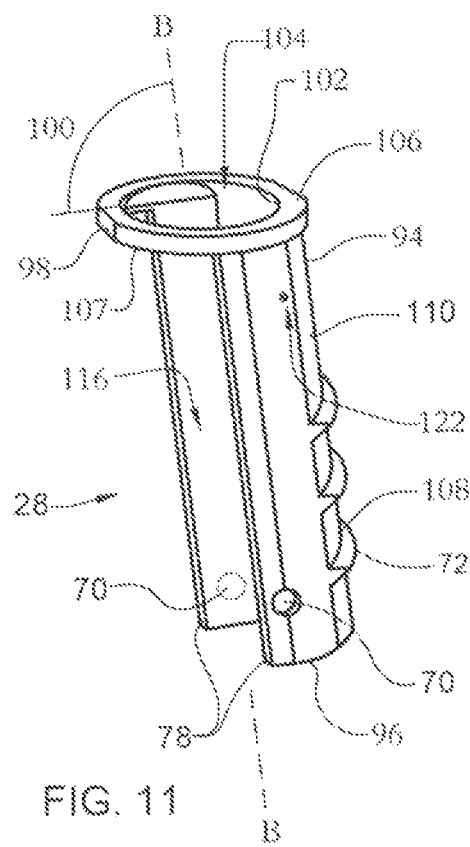
FIG. 11 is a perspective view of a component of the system shown in FIG. 1.

Second vertical member 28 extends along a longitudinal axis B between a first end 94 and an opposite second end 96 of second vertical member 28, as shown in FIG. 11, for example. First end 94 of second vertical member 28 comprises a lip 98 extending at an angle 100 relative to axis B. Lip 98 is configured for engagement with end surface 52 of top nut 24 to move cannula 22 between narrowed and expanded configurations, as will be discussed. Lip 98 comprises an inner surface 102 defining an opening 104 of second vertical member 28. In some embodiments, opening 104 has a circular cross sectional configuration and lip 98 comprises opposite planar upper and lower surfaces 106, 107 that extend parallel to one another. Lip 98 may be disposed at alternate orientations, relative to axis B, such as, for example, transverse, perpendicular and/or other angular orientations such as acute or obtuse, co-axial and/or may be offset or staggered. Angle 100 can be an acute angle, for example between about 45 and about 90 degrees.

Figure 12:
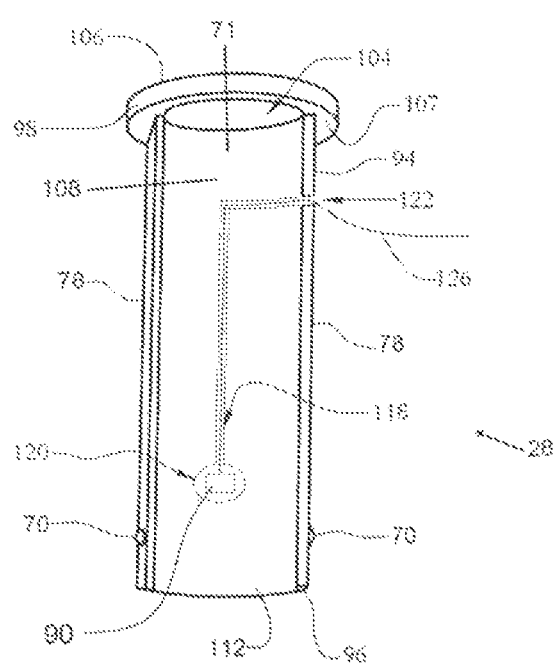
FIG. 12 is a perspective view of a component of the system shown in FIG. 1.

Second vertical member 28 comprises an arcuate portion 108 that extends between side walls 78 of second vertical member 28, as shown in FIG. 12, for example. Arcuate portion 108 comprises an outer surface 110 that is convexly curved between side walls 78 and an inner surface 112 and opposite outer surface 110 that is concavely curved between side walls 78 of second vertical member 28, as shown in FIG. 9, for example. Each of the side walls 78 may comprise at least one protrusion 70 that extends outwardly therefrom and may be positioned adjacent second end 96 of second vertical member 28. In some embodiments, protrusions 70 each have a hemispherical configuration that matches that of recesses 68 of first vertical member 26.

Inner surfaces 102, 112 of lip 98 and arcuate portion 108 of second vertical member 28 and inner surfaces of side walls 78 of second vertical member 28 define a conduit 116 of second vertical member 28, as shown in FIGS. 5A and 9-11, for example. In some embodiments, cannula 22 is made entirely of radiopaque materials to aid in fluoroscopic visualization. In some embodiments, only a distal tip of second vertical member 28 is radiopaque to aid in fluoroscopic visualization.

Figure 13:
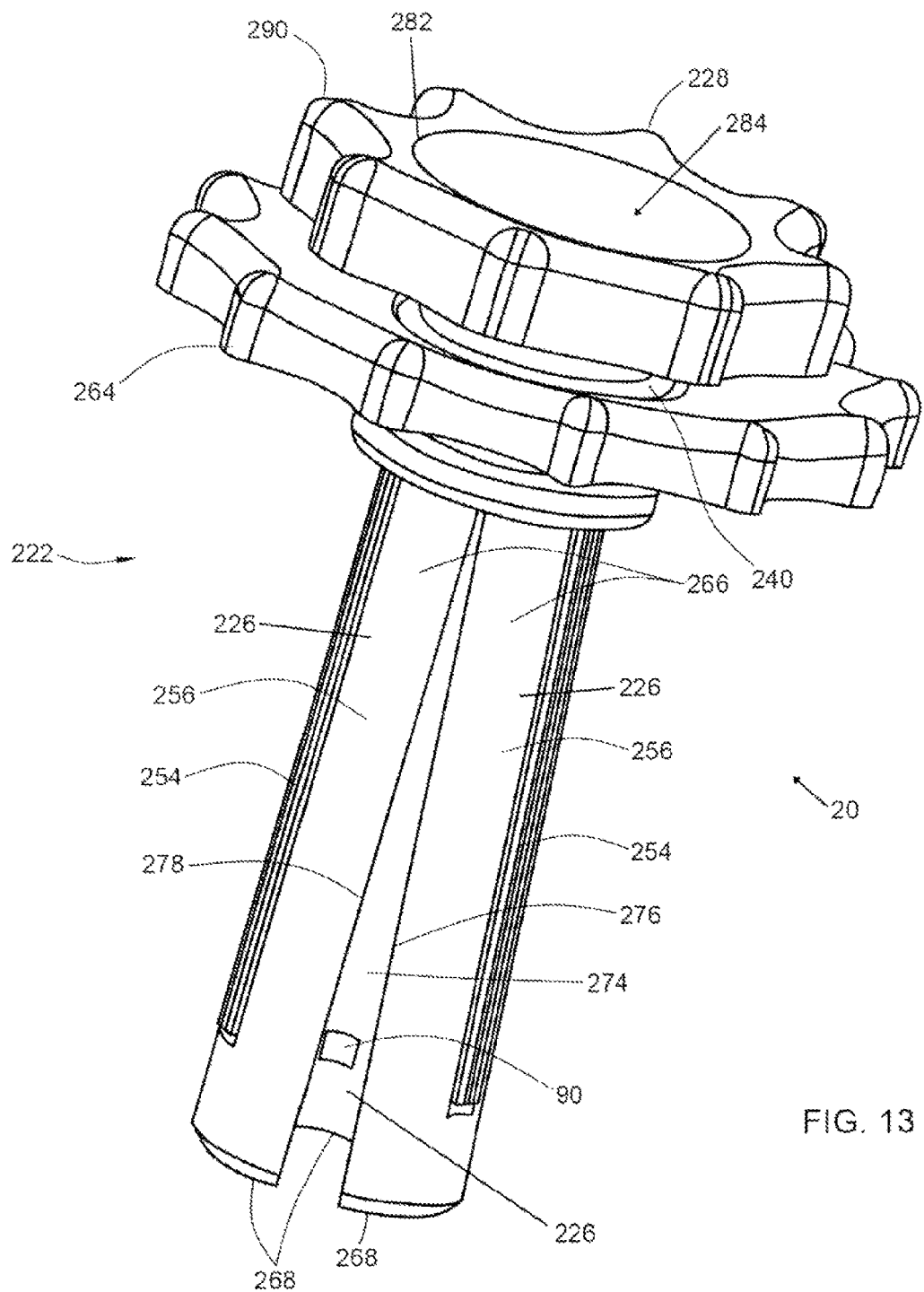
FIG. 13 is a perspective view of one embodiment of the surgical system, in accordance with the principles of the present disclosure.
Figure 17:
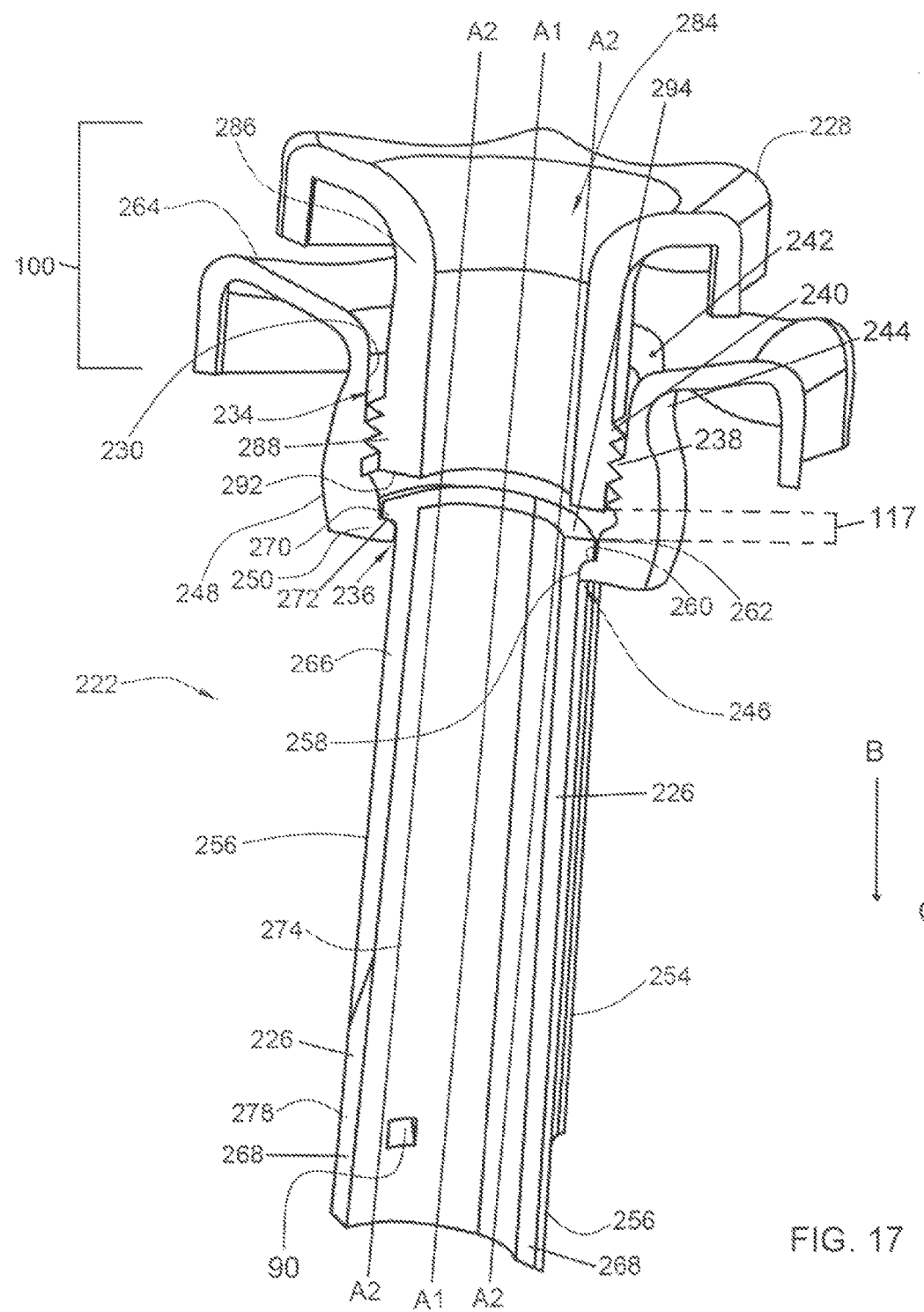
FIG. 17 is a perspective, cross sectional view of components of the embodiment shown in FIG. 13.

In FIG. 13, the surgical instrument 20 comprises a handling portion 100, as shown in FIG. 17, within which is a control junction 117, and a top nut 228. There is also a plurality of vertical members 226 operatively attached to the control junction 117 at their proximal ends 266. The handling portion 100, as shown in FIG. 17, comprises gripping portion 264. In one embodiment, gripping portion 264 is a telescopic relationship to the top nut 228, which is movable relative to the gripping portion 264. A telescopic relationship means that at least a portion of the top nut 228 is slidably disposed within the gripping portion 264. The telescopic relationship can provide a sealingly fit connection and may be achieved using inclined planes or threading, for example.

Figure 14:
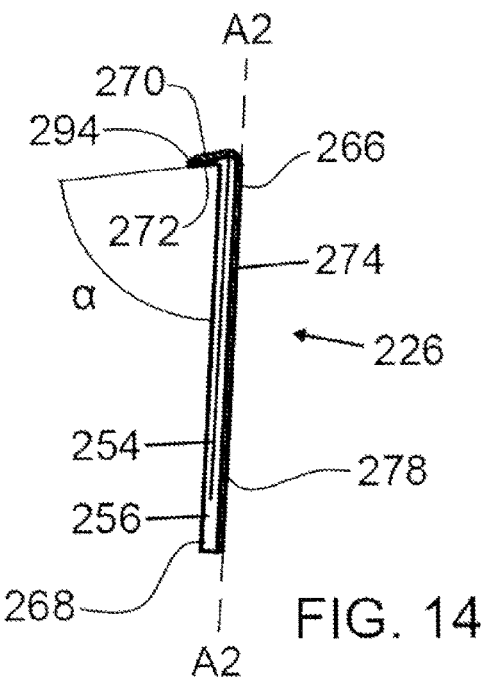
FIG. 14 is a perspective view of a component of the embodiment shown in FIG. 13.

Cannula 222 comprises a gripping portion 264, a plurality of vertical members 226 and a top nut 228, as shown in FIG. 13, for example. Vertical members 226, one of which is shown in FIG. 14, are positioned within gripping portion 264, shown in FIGS. 15A-15C to produce the structure shown in FIGS. 16A and 16B. Top nut 228 is configured to engage the gripping portion 264 at the control junction 117, as shown in FIG. 17, to produce the structure shown in FIGS. 13 and 17. Top nut 228 may be rotated relative to gripping portion 264 such that cannula 222 moves from the configuration shown in FIGS. 16A and 17 to the configuration shown in FIGS. 13, 21 and 22. When cannula 222 is in the configuration shown in FIGS. 16A and 17, vertical members 226 extend parallel to one another and when cannula 222 is in the configuration shown in FIGS. 13, 21 and 22, vertical members 226 extend transverse to one another, as will be discussed.

Figures 15A, 15B:
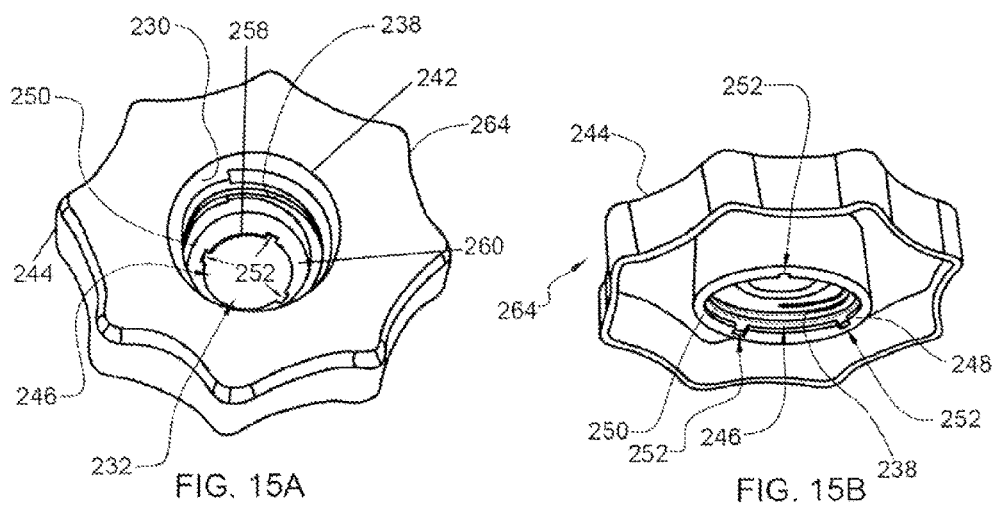
FIG. 15A is a top, perspective view of a component of the embodiment shown in FIG. 13.
FIG. 15B is a bottom, perspective view of a component of the embodiment shown in FIG. 13.
Figure 15C:
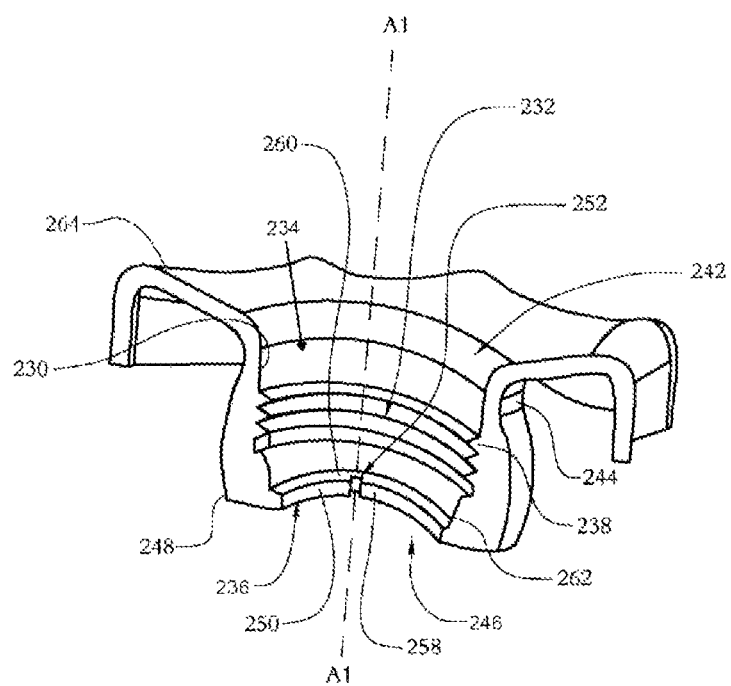
FIG. 15C is a perspective, cross sectional view of a component of the embodiment shown in FIG. 13.

Gripping portion 264 comprises an inner surface 230 defining a passageway 232, as shown in FIG. 15A, for example. Passageway 232 comprises a proximal portion 234 and a distal portion 236, as shown in FIG. 15C, for example. Proximal portion 234 has a maximum diameter that is greater than that of distal portion 236. Proximal portion 234 comprises an interior thread form 238 configured to engage an exterior thread form 240 of top nut 228 so as to couple gripping portion 264 with top nut 228, as will be discussed. Interior thread form 238 and/or exterior thread form 240 can have various pitches.

Passageway 232 of gripping portion 264 extends through an opening 242 in a proximal end 244 of gripping portion 264, as shown in FIGS. 15A and 15C, for example. Passageway 232 also extends through an opening 246 in a distal end 248 of gripping portion 264, as also shown in FIGS. 15A and 15C, for example. Openings 242 and 246 of gripping portion 264 can be substantially circular. Passageway 232 of gripping portion 264 defines a first longitudinal axis A1 extending between proximal end 244 and distal end 248 of gripping portion 264.

Opening 246 of gripping portion 264 is defined by an annular flange 250, as shown in FIGS. 15A-15C, for example. In some embodiments, flange 250 extends perpendicular to axis A1 and may comprise one or a plurality of slots 252. Slots 252 of flange 250 are configured for disposal of a ridge 254 projecting from an outer surface 256 of vertical member 226, as will be discussed. Slots 252 are disposed radially about flange 250 and are spaced apart from one another. In one embodiment, slots 252 are evenly spaced apart from one another. Slots 252 may each have a depth that is substantially equivalent to a height of each of ridges 254 such that outer surface 256 of vertical member 226 engages an inner surface 258 of flange 250 that defines opening 246 of gripping portion 264. In some embodiments, inner surface 258 of flange 250 is continuously curved between adjacent slots 252 of flange 250 of gripping portion 264.

Flange 250 comprises a top surface 260 that extends perpendicular to axis A1 and abuts an inner wall 262 of gripping portion 264, as shown in FIG. 15C, for example. In some embodiments, inner wall 262 extends perpendicular to top surface 260 such that inner wall 262 extends parallel to axis A1. In some embodiments, distal end 248 of gripping portion 264 comprises a gripping portion 264 configured for gripping by a medical practitioner to selectively rotate gripping portion 264 about axis A1.

Vertical members 226 are positioned in passageway 232 of gripping portion 264. In one embodiment, cannula 222 comprises three vertical members 226. In some embodiments, cannula 222 comprises six vertical members 226. In embodiments that comprise more than one vertical member 226, vertical members 226 are each positioned in passageway 232 of gripping portion 264 and each extend along a second longitudinal axis A2 between a proximal end 266 and an opposite distal end 268, as shown in FIG. 14, for example. Proximal ends 266 each comprise a lip 270 extending at an angle α relative axis A2. A bottom surface 272 of each lip 270 of vertical members 226 engages top surface 260 of flange 250 of gripping portion 264 to couple vertical members 226 with gripping portion 264, as shown in FIG. 17, for example. Angle α may be an acute angle and lip 270 may be disposed at alternate orientations, relative to axis A2, such as, for example, transverse, perpendicular and/or other angular orientations such as acute or obtuse, co-axial and/or may be offset or staggered.

Figure 16A:
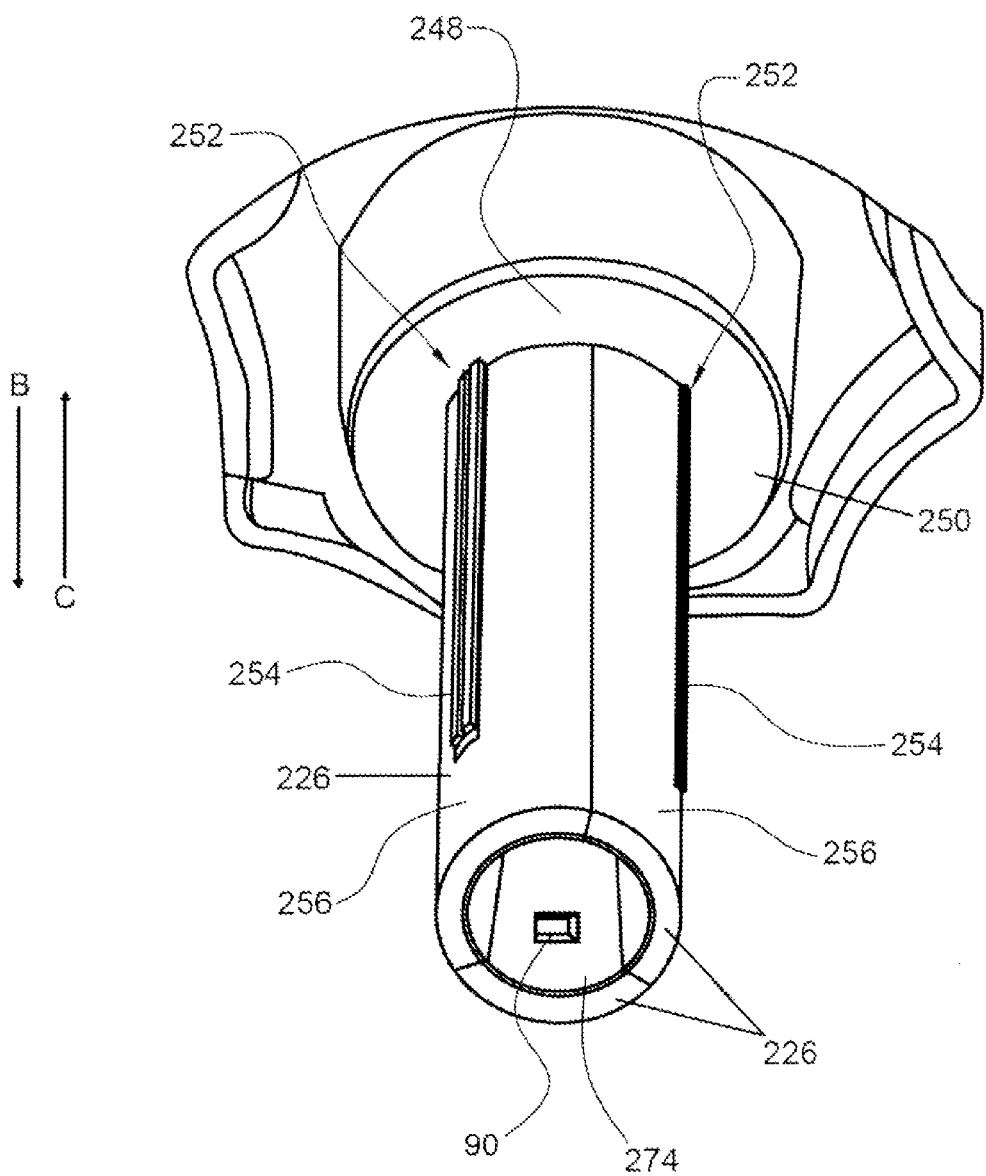
FIG. 16A is a perspective, bottom view of components of the embodiment shown in FIG. 13.
Figure 16B:
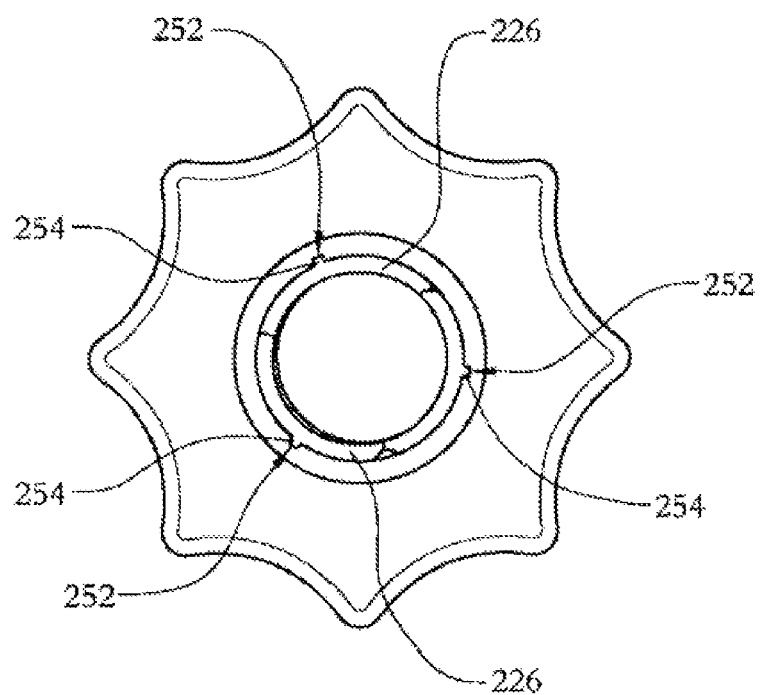
FIG. 16B is a top view of components of the embodiment shown in FIG. 13.

Vertical members 226 comprises one or more ridges 254 and may be positioned in one of slots 252 of flange 250 of gripping portion 264, as shown in FIGS. 16A and 16B, for example. Positioning ridges 254 in slots 252 prevents vertical members 226 from rotating relative to gripping portion 264. When ridges 254 are positioned in slots 252, vertical members 226 are movable along axis A1 in the direction shown by arrow B in FIG. 16A and the direction shown by arrow C in FIG. 16A. Outer surfaces 256 of vertical members 226 slide along inner surface 258 of flange 250 as vertical members 226 move along axis A1 in the direction shown by arrow B or the direction shown by arrow C. Vertical members 226 are movable along axis A1 in the direction shown by arrow B until bottom surfaces 272 of lips 270 of vertical members 226 engage top surface 260 of flange 250 of gripping portion 264.

Figure 18:
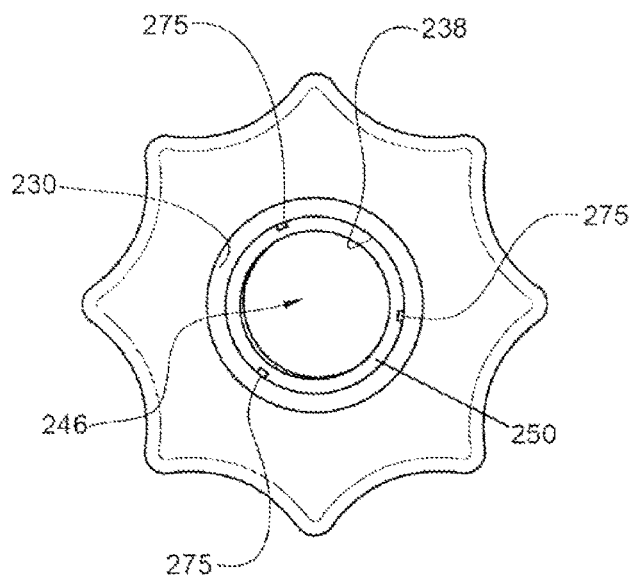
FIG. 18 is a top view of one embodiment of a component of the embodiment shown in FIG. 13.
Figure 19:
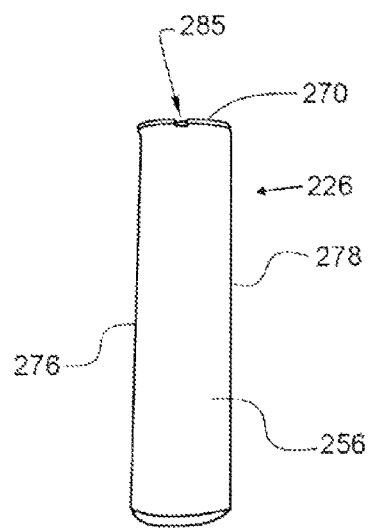
FIG. 19 is a side view of one embodiment of a component of the embodiment shown in FIG. 13.
Figure 20:
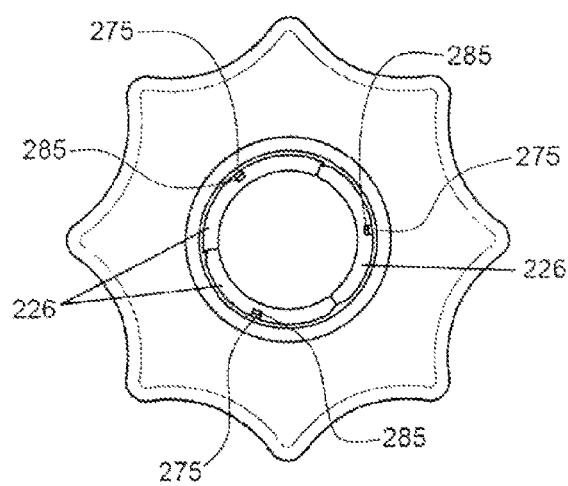
FIG. 20 is a top view of one embodiment of components of the embodiment shown in FIG. 13.

In one embodiment, shown in FIGS. 18-20, gripping portion 264 does not include slots 252 such that opening 246 of gripping portion 264 is continuously curved and has a circular cross section. Flange 250 of gripping portion 264 comprises a plurality of spaced apart projections 275. In some embodiments, projections 275 of flange 250 extend parallel to axis A1 and are disposed radially about flange 250. Projections 275 can be either be evenly or unevenly spaced apart from one another. The number of projections 275 is equal to at least the number of vertical members 226.

As shown in FIGS. 18-20, vertical members 226 may not include ridges 254 such that outer surfaces 256 of vertical members 226 are continuously curved between axial surfaces 276, 278 of vertical members 226. In the embodiment shown in FIGS. 18-20, lips 270 of vertical members 226 each comprise a cutout 285. Cutouts 285 of vertical members 226 are configured for disposal of at least one of projections 275 of flange 250, as shown in FIG. 20, to prevent vertical members 226 from rotating relative to gripping portion 264. In some embodiments, projections 275 may be disposed at alternate orientations, relative to axis A1, such as, for example, transverse, perpendicular and/or other angular orientations such as acute or obtuse, co-axial and/or may be offset or staggered.

Figure 21:
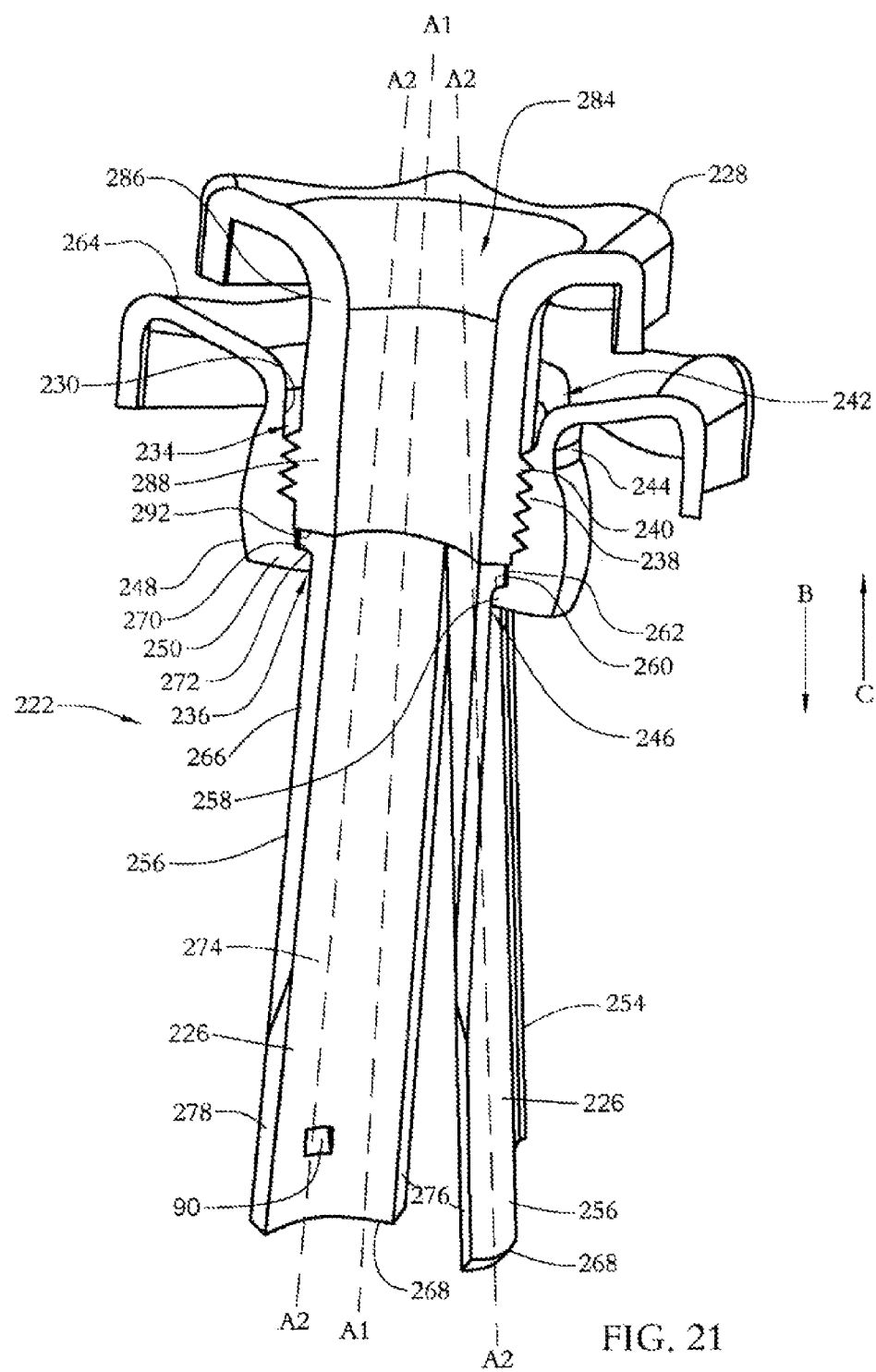
FIG. 21 is a perspective, cross sectional view of components of the embodiment shown in FIG. 13.

Vertical members 226 each comprise an inner surface 274 that is concavely curved between axial end surfaces 276, 278 of vertical members 226, as shown in FIG. 21, for example. In some embodiments, cannula 222 comprises material, for example fabric, between and/or around vertical members 226 so as to form a sheath or sleeve around vertical members 226 that allows vertical members 226 to move between narrowed and expanded configurations discussed below. That is, the material may be wrapped around vertical members 226 to block and/or cover openings between vertical members 226 as cannula 222 moves between the narrowed and expanded configurations as discussed below.

Top nut 228 is positioned in proximal portion 234 of passageway 232 of gripping portion 264 such that exterior thread form 240 of top nut 228 engages interior thread form 238 of gripping portion 264, as shown in FIGS. 17 and 21, for example. Top nut 228 is rotatable relative to gripping portion 264 about axis A1 in a first direction. As top nut 228 is rotated in the first direction it moves relative to gripping portion 264 in the direction shown by arrow B in FIGS. 17 and 21. As top nut 228 is rotated relative to gripping portion 264 about axis A1 in a second direction opposite the first direction, such as, for example, clockwise or counterclockwise, top nut 228 moves relative to gripping portion 264 in the direction shown by arrow C in FIGS. 17 and 21.

Figure 23A:
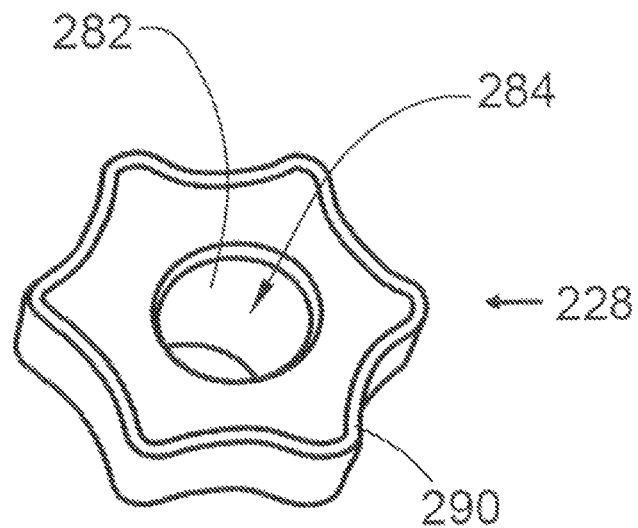
FIG. 23A is a top, perspective view of a component of the embodiment shown in FIG. 13.
Figure 23B:
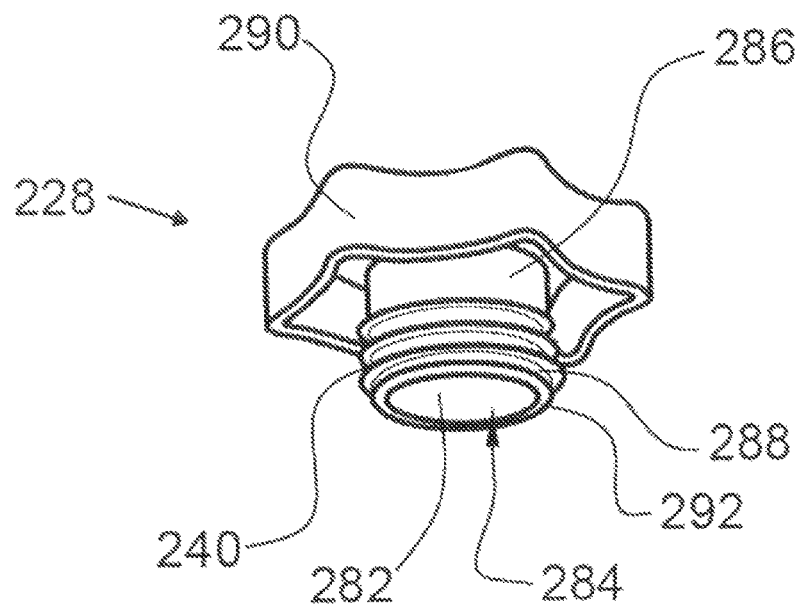
FIG. 23B is a perspective view of a component of the embodiment shown in FIG. 13.

An inner surface 282 of top nut 228 defines a lumen 284, shown in FIGS. 23A and 23B, for example. Top nut 228 comprises a first end 286 and an opposite second end 288, as shown in FIG. 23B, for example. First end 286 of top nut 228 comprises a gripping portion 290 configured for gripping by a medical practitioner to selectively rotate top nut 228 about axis A1. Second end 288 of top nut 228 comprises a planar end surface 292 configured to engage top surfaces 294 of lips 270. In some embodiments, end surface 292 of top nut 228 extends perpendicular to axis A1. In some embodiments, end surface 292 may be disposed at alternate orientations, relative to axis A1, such as, for example, transverse, perpendicular and/or other angular orientations such as acute or obtuse, co-axial and/or may be offset or staggered.

To assemble cannula 222, vertical members 226 are positioned within gripping portion 264 to produce the structure shown in FIGS. 16A and 16B. Top nut 228 is positioned within proximal portion 234 of passageway 232 of gripping portion 264 such that exterior thread form 240 of top nut 228 engages interior thread form 238 of gripping portion 264 to produce the structure shown in FIG. 13. In FIG. 17, when cannula 222 is in a narrowed configuration, end surface 292 of top nut 228 is spaced apart from top surfaces 294 of vertical members 226 and axes A2 extend parallel to axis A1, for example. In some embodiments, end surface 292 of top nut 228 engages top surfaces 294 of vertical members 226 when cannula 222 is in the narrowed configuration, but does not push down upon top surfaces 294 of vertical members 226 with sufficient force to cause vertical members 226 to move relative to gripping portion 264 and/or one another such that axes A2 extend parallel to axis A1.

To move cannula 222 from the narrowed configuration, shown in FIG. 17, to an expanded configuration, shown in FIG. 21, top nut 228 is rotated relative to gripping portion 264 about axis A1 in a first direction, such as, clockwise or counterclockwise. Rotating top nut 228 relative to gripping portion 264 about axis A1 in the first direction causes top nut 228 to move relative to gripping portion 264 along axis A1 in the direction shown by arrow B in FIGS. 17 and 21. Top nut 228 is rotated relative to gripping portion 264 about axis A1 in the first direction until end surface 292 of top nut 228 engages top surfaces 294 of vertical members 226 such that end surface 292 of top nut 228 pushes down upon top surfaces 294 with sufficient force to cause vertical members 226 to deflect outwardly from axis A1 such that axes A2 each extend transverse to axis A1, as shown in FIG. 21, for example.

Figure 26:
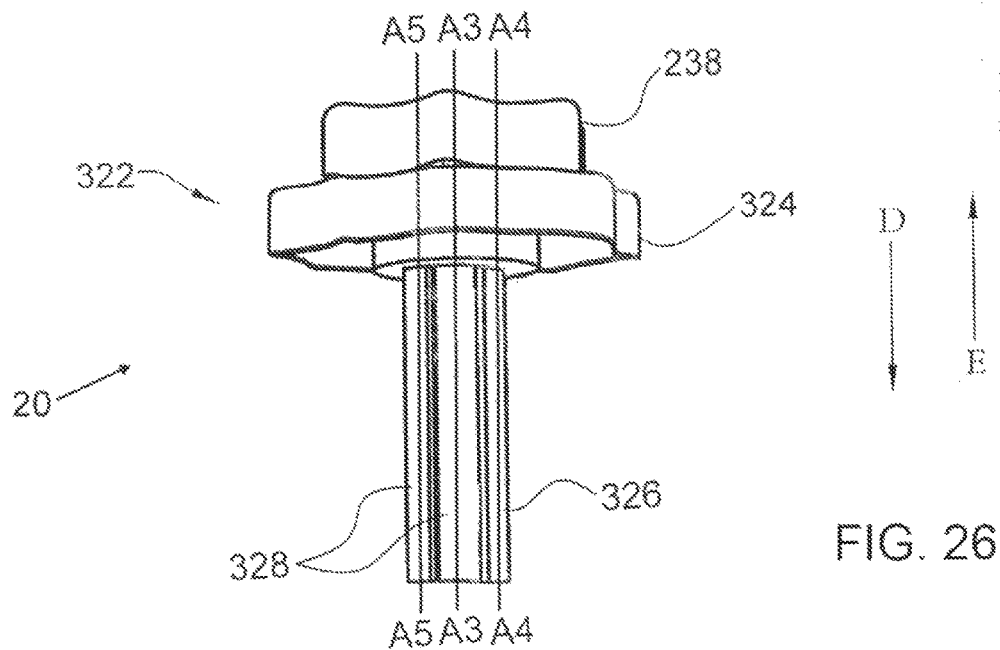
FIG. 26 is a side view of one embodiment of the surgical system, in accordance with the principles of the present disclosure.
Figure 27:
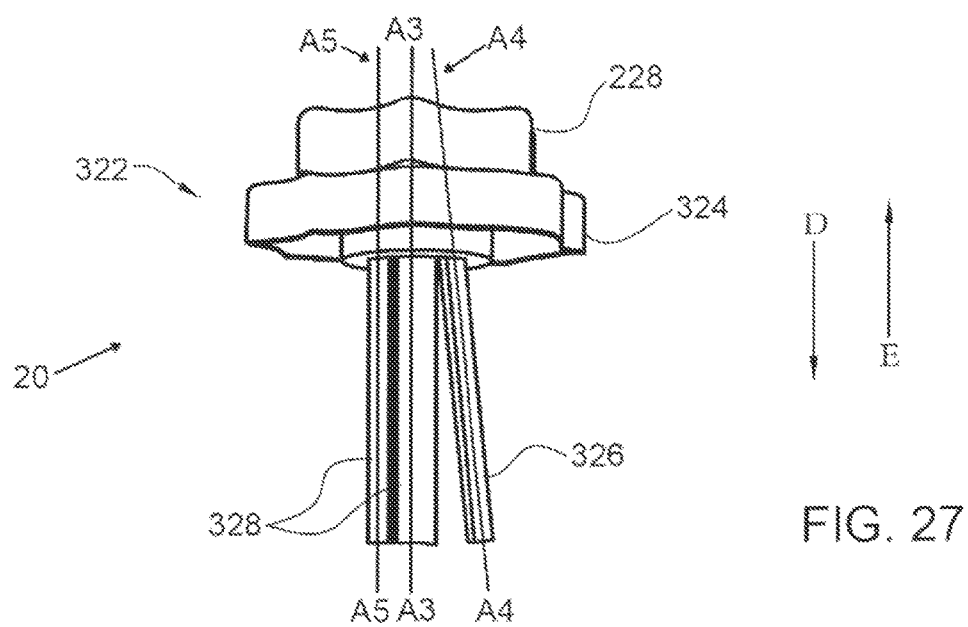
FIG. 27 is a side view of components of the embodiment shown in FIG. 26.
Figure 28:
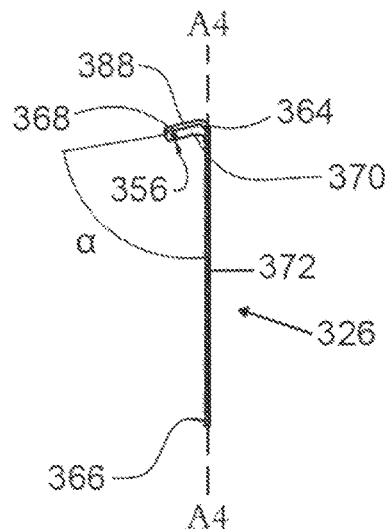
FIG. 28 is a side view of a component of the embodiment shown in FIG. 26.
Figure 29:
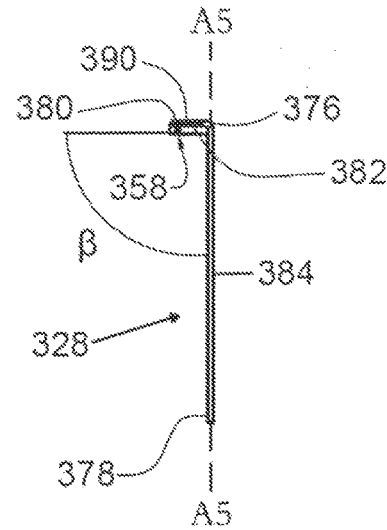
FIG. 29 is a side view of a component of the embodiment shown in FIG. 26.

Turning now to FIGS. 26-35. FIGS. 26-35 illustrate components of a surgical device of surgical system 20, such as, for example, a cannula 322 in accordance with the principles of the present disclosure. As with cannulas 22 and 222, cannula 322 comprises a gripping portion 324, a plurality of vertical members 326, a plurality of vertical members 328 and top nut 228, as shown in FIGS. 26 and 27, for example. Vertical members 326, one of which is shown in FIG. 28, and vertical members 328, one of which is shown in FIG. 29, are positioned within gripping portion 324, shown in FIGS. 30 and 31 to produce the structure shown in FIGS. 32 and 33. Top nut 228 engages gripping portion 324 to produce the structure shown in FIG. 26. Top nut 228 may be rotated relative to gripping portion 324 such that cannula 322 moves from the configuration shown in FIG. 26 to the configuration shown in FIG. 27. When cannula 322 is in the configuration shown in FIG. 26, vertical members 326, 328 extend parallel to one another and when cannula 322 is in the configuration shown in FIG. 27, vertical members 326 extend transverse to vertical members 328, as will be discussed.

Figure 30:
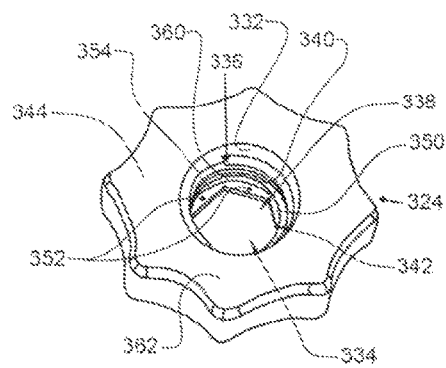
FIG. 30 is a top, perspective view of a component of the embodiment shown in FIG. 24.
Figure 30A:
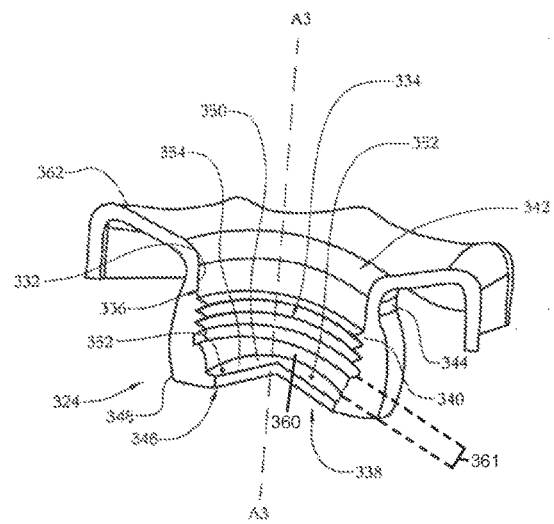
FIG. 30A is a perspective, cross sectional view of a component of the embodiment shown in FIG. 26.

Gripping portion 324 comprises an inner surface 332 defining a passageway 334, shown in FIG. 30, for example. Passageway 334 comprises a proximal portion 336 and a distal portion 338, as shown in FIG. 30A, for example. Proximal portion 336 of passageway 334 has a maximum diameter that is greater than that of distal portion 338 of passageway 334. FIG. 30A also shows a control junction 361 configured to receive the lips 368 and 380. Proximal portion 336 comprises an interior thread form 340 that is configured to engage thread form 240 of top nut 228 so as to couple gripping portion 324 with top nut 228, as will be discussed. Passageway 334 extends through an opening 342 in a proximal end 344 of gripping portion 324 and an opening 346 in a distal end 348 of gripping portion 324, as shown in FIG. 30, for example. Passageway 334 defines a longitudinal axis A3 extending between proximal end 344 of gripping portion 324 and distal end 348 of gripping portion 324. Opening 342 can be circular or polygonal.

Figure 31:
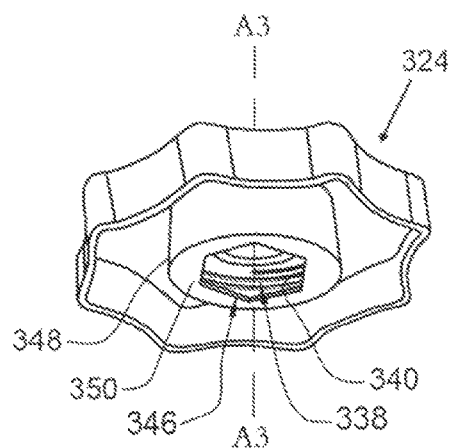
FIG. 31 is a bottom, perspective view of a component of the embodiment shown in FIG. 26.

Distal portion 338 of passageway 334 and opening 346 are defined, at least in part, by an annular flange 350 of gripping portion 324, as shown in FIGS. 30, 30A and 31, for example. In some embodiments, flange 350 extends perpendicular to axis A3 and comprises one or a plurality of projections 352 extending from a top surface 354 of flange 350, as shown in FIGS. 30 and 30A, for example. In some embodiments, projections 352 are cylindrical and are each configured for disposal in throughholes 356 of vertical members 326 or throughholes 358 of vertical members 328 to prevent vertical members 326, 328 from rotating relative to gripping portion 324, as will be discussed. In some embodiments, at least one of projections 352 extends parallel to axis A3. Top surface 354 of flange 350 abuts an inner wall 360 of gripping portion 324 and extends perpendicular to axis A3. In some embodiments, inner wall 360 of gripping portion 324 extends perpendicular to top surface 354 of flange 350 such that inner wall 360 of gripping portion 324 is parallel with axis A3. Proximal end 344 of gripping portion 324 may comprise a gripping portion 362 configured for gripping by a medical practitioner to selectively rotate gripping portion 324 about axis A3.

Figure 32:
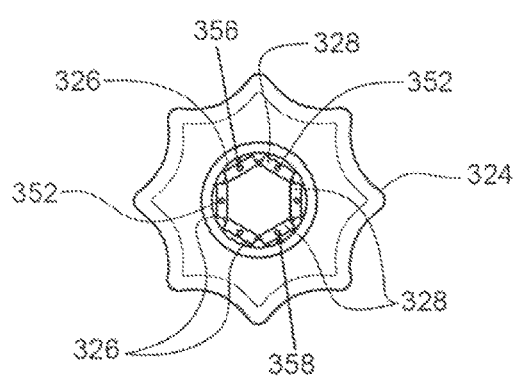
FIG. 32 is a top view of components of the embodiment shown in FIG. 26.

Vertical members 326 each extend along a longitudinal axis A4 between a first end 364 and an opposite second end 366, as shown in FIG. 28, for example. Vertical members 326 each comprise a lip 368 extending at an angle α relative to a respective axis A4. Vertical members 326 are positioned in passageway 334 of gripping portion 324 such that a bottom surface 370 of each lip 368 engages top surface 354 of flange 350 of gripping portion 324 and is disposed within control junction 361. Vertical members 326 are positioned relative to gripping portion 324 such that projections 352 of flange 350 of gripping portion 324 extend through throughholes 356 of vertical members 326, as shown in FIG. 32, to prevent the vertical members 326 from rotating relative to gripping portion 324. In some embodiments, angle α is an acute angle and lip 368 may be disposed at alternate orientations, relative to axis A4, such as, for example, transverse, perpendicular and/or other angular orientations such as acute or obtuse, co-axial and/or may be offset or staggered. Cannula 322 comprises one or a plurality of vertical members 326, about 2 to about 10 vertical members, for example may be used.

Vertical members 328 each extend along a longitudinal axis A5 between a first end 376 and an opposite second end 378, as shown in FIG. 29, for example. Vertical members 328 each comprise a lip 380 extending at an angle β relative to axis A5 that is different than angle α. Vertical members 328 are positioned in passageway 334 of gripping portion 324 such that a bottom surface 382 of each lip 380 engages top surface 354 of flange 350 of gripping portion 324. Vertical members 328 are positioned relative to gripping portion 324 such that projections 352 of flange 350 extend through throughhole 358 of vertical members 328, as shown in FIG. 31, so as to prevent the vertical members 328 from rotating relative to gripping portion 324. Angle β may be 90 degrees such that lip 380 extends perpendicular to axis A5.

In the alternative, angle β may be an acute angle for example between 45 and 90 degrees. Lip 380 may be disposed at alternate orientations, relative to axis A5, such as, for example, transverse, perpendicular and/or other angular orientations such as acute or obtuse, co-axial and/or may be offset or staggered. As with cannulas 22 and 222, cannula 322 discussed herein may comprise one or a plurality of vertical members 328. In one embodiment, cannula 322 may comprise three vertical members 326 and three vertical members 328.

Top nut 228 is rotatably disposed in passageway 334 of gripping portion 324 such that exterior thread form 238 of top nut 228 engages interior thread form 340 of gripping portion 324. As with cannulas 22 and 222 rotating top nut 228 relative to gripping portion 324 about axis A3 in a first direction moves top nut 228 relative to gripping portion 324 in the direction shown by arrow D in FIGS. 26 and 27. Rotating top nut 228 relative to gripping portion 324 about axis A3 in an opposite second direction moves top nut 228 in the direction shown by arrow E in FIGS. 26 and 27. Lumen 284 of top nut 228 is in communication with passageway 334 of gripping portion 324. End surface 292 of top nut 228 may be configured to engage top surfaces 388 of lips 368 of vertical members 326 and top surfaces 390 of lips 380 of vertical members 328.

Figure 33:
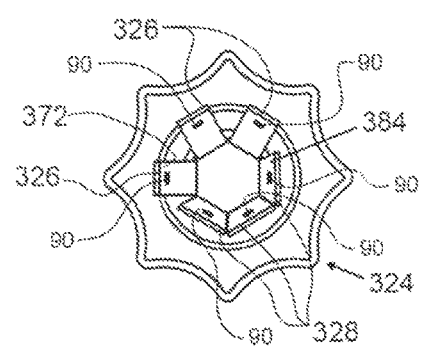
FIG. 33 is a bottom view of components of the embodiment shown in FIG. 26.

To assemble cannula 322, vertical members 326, 328 are positioned within gripping portion 324 such that bottom surfaces 370 of vertical members 326 and bottom surfaces 382 of vertical members 328 engage top surface 354 of flange 350 of gripping portion 324 to produce the structure shown in FIGS. 32 and 33. Top nut 228 is positioned within proximal portion 336 of passageway 334 such that exterior thread form 240 of top nut 228 engages interior thread form 340 of gripping portion 324 to produce the structure shown in FIG. 26. When cannula 322 is in a narrowed configuration, end surface 292 of top nut 228 may be spaced apart from top or rest on surfaces 388 of vertical members 326 and top surfaces 390 of vertical members 328 such that axes A3, A4 and A5 extend parallel to one another, as shown in FIG. 26, for example.

To move cannula 322 from the narrowed configuration, shown in FIG. 26, to an expanded configuration, shown in FIG. 27, top nut 228 is rotated relative to gripping portion 324 about axis A3 in a first direction causing top nut 228 to move relative to gripping portion 324 along axis A1 in the direction shown by arrow D in FIGS. 26 and 27. Top nut 228 is rotated relative to gripping portion 324 about axis A3 in the first direction until end surface 292 of top nut 228 pushes down upon top surfaces 388 of vertical members 326 with sufficient force to cause vertical members 326 to deflect outwardly from axis A3 such that axes A4 each extend transverse to axes A3, A5, as shown in FIG. 27, for example.

The vertical members of the present invention may comprise illumination. For example, cannula 22, cannula 222 and/or cannula 322 may comprise at least one light source 90, such as for example, a light emitting diode (LED). Light source 90 may be variously positioned in cannula 22, cannula 222 and/or cannula 322 so as to provide illumination and limit shadowing. In some embodiments, cannula 22, cannula 222 and/or cannula 322 comprises at least one light source 90 on top and/or bottom portions of the vertical members so as to reduce shadowing.

In one embodiment, cannula 22 comprises light source 90 in or on first vertical member 26 and is configured to illuminate at least a portion of passageway 66 of first vertical member 26. Light source 90 may be permanently fixed or may be configured to be removable from first vertical member 26. In some embodiments, light source 90 is embedded within the wall of the first vertical member 26 where at least a portion of first vertical member 26 is transparent or translucent so as to allow light from light source 90 to pass through first vertical member 26 to illuminate the cannula passageway while reducing shadowing within the passageway. In some embodiments, cannula 22 comprises one of more light sources 90 and is powered by a battery or other external power source.

In some embodiments, outer surface 71 of first vertical member 26 of cannula 22 comprises a port 84, shown in FIGS. 1A, 5A and 7, for example. Port 84 comprises an opening 85 that is in communication with a lumen 86 defined by inner surface 60 of first vertical member 26, shown in FIGS. 1A and 5A, for example. Lumen 86 extends into inner surface 60 of first vertical member 26 without extending through outer surface 71 of first vertical member 26. Lumen 86 terminates in a cavity 88 that extends into inner surface 60 without extending through outer surface 71, as shown in FIG. 2B, for example. Light source 90 is positioned in cavity 88 of first vertical member 26 such that a wire 92 connected to light source 90 extends through port 84 of first vertical member 26, as shown in the combination of FIGS. 2B and 3, for example. In some embodiments, wire 92 is used to provide power to light source 90 of first vertical member 26.

In some embodiments, second vertical member 28 of cannula 22 also comprises light source 90. Light source 90 is positioned to illuminate at least a portion of conduit 116 of second vertical member 28. As in first vertical member 26, light source 90 may be permanently fixed to or embedded with the wall of second vertical member 28. In the embodiment where light source 90 is embedded in the wall of second vertical member 28, at least of portion of second vertical member 28 is transparent or translucent so as to allow light from light source 90 to pass through the wall of second vertical member 28.

In some embodiments, inner surface 112 of arcuate portion 108 of second vertical member 28 defines a lumen 118 that terminates in a cavity 120 that extends into inner surface 112 without extending through outer surface 110 of arcuate portion 108, as shown in FIG. 12, for example. Lumen 118 is in communication with an aperture 122 extending through inner and outer surfaces of one of side walls 78 of second vertical member 28. Lumen 118 extends into inner surface 112 of arcuate portion 108 without extending through outer surface 110 of second vertical member 28, as shown in FIG. 12, for example. Light source 90 may be positioned in cavity 120 such that a wire 126 connected to light source 90 extends through lumen 118 and aperture 122 of second vertical member 28. In some embodiments, wire 126 is used to provide power to light source 90 of second vertical member 28.

The same or similar lighting configurations may also be present in cannula 222. In some embodiments, inner surfaces 274 of vertical members 226 of cannula 222 comprise light source 90 at distal end 268 of vertical member 226. Light source 90 is configured and positioned to project light away from inner surface 274 so as to reduce shadowing and provide improved illumination. All or at least one vertical member 226 comprises a light source 90 that may comprise a power source, such as, for example, a battery to provide power to light sources 90 of vertical members 226. In some embodiments, light sources 90 are powered by an external power source and comprise a switch to turn each of light sources 90 on and off.

The same or similar lighting configurations may also be present in cannula 322. In one embodiment, at least one of vertical members 326 may comprise a light source 90 at the proximal end and/or at the distal end, as shown in FIG. 33, for example. Light sources 90 are each configured to project light away from inner surface 372 of vertical member 326 and may be turned on and off as needed. The direction of the light source 90 as well as its intensity is designed for maximum illumination while reducing the occurrence of shadowing.

In some embodiments, at least one of vertical members 328 comprises an inner surface 384 that comprises light source 90, as shown in FIG. 33, for example. Light sources 90 of vertical members 328 are each configured to project light away from inner surface 384 and may comprise a power source, such as, for example, a battery to provide power to at least one of light sources 90. In the alternative, light sources 90 of vertical members 328 may be powered by an external power source and may comprise an on/off switch to allow the medical practitioner to use the light source when needed.

As stated above, cannulas 22, 222 and/or 322 are configured to help prevent dorsal movement thereof caused by movement of a patient or involuntary muscle contraction of an awake and/or at least partially conscious patient. That is, cannulas 22, 222 and/or 322 may comprise an outer thread form 72 configured to anchor the cannula to surrounding tissue, for example muscle, so as to prevent unintended movement of cannulas 22, 222 and/or 322. When cannulas 22, 222 and/or 322 face dorsal forces, cannulas 22, 222 and/or 322 are capable of expanding, thus further securing cannulas 22, 222 and/or 322 in place.

In some embodiments, an outer surface 71 of first vertical member 26 of cannula 22 comprises outer thread form 72, shown in FIGS. 1, 1A and 2B, for example. In some embodiments, outer surface 110 of arcuate portion 108 of second vertical member 28 of cannula 22 comprises an outer thread form 72, shown in FIGS. 1, 1A, 3, 5, 5A and 11, for example. Outer thread forms 72 of first and second vertical members 26, 28 are configured to mate with tissue so as to fix cannula 22 relative to the anatomy of a patient. Outer thread form 72 may have different pitches and number of turns.

Figure 19A:
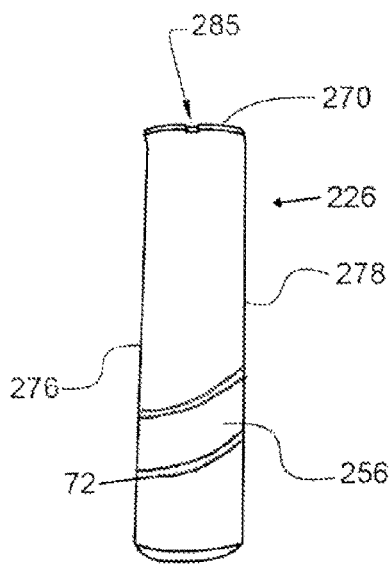
FIG. 19A is a side view of one embodiment of a component of the embodiment shown in FIG. 13.
Figure 24:
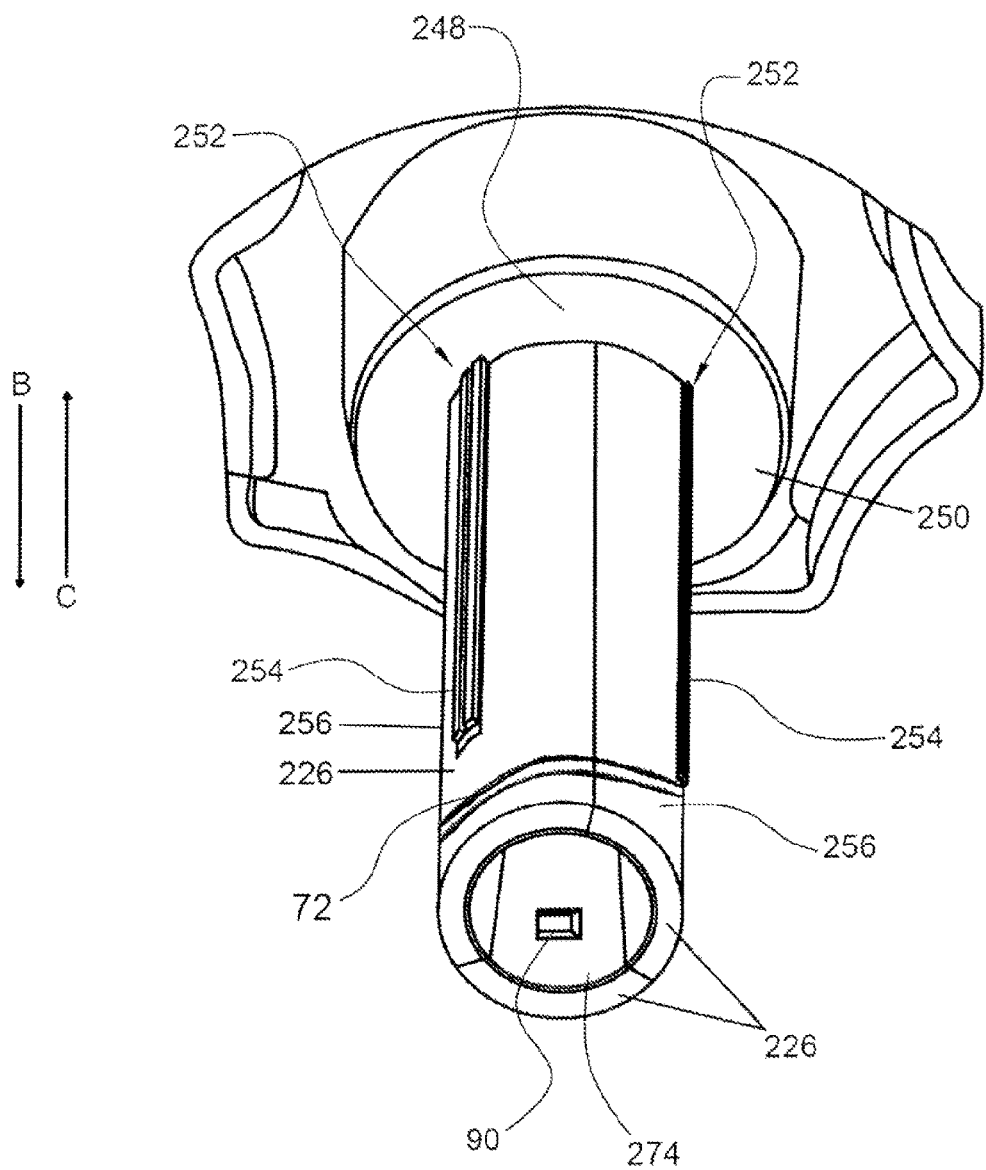
FIG. 24 is a perspective, bottom view of components of one embodiment of the embodiment shown in FIG. 13.
Figure 25:
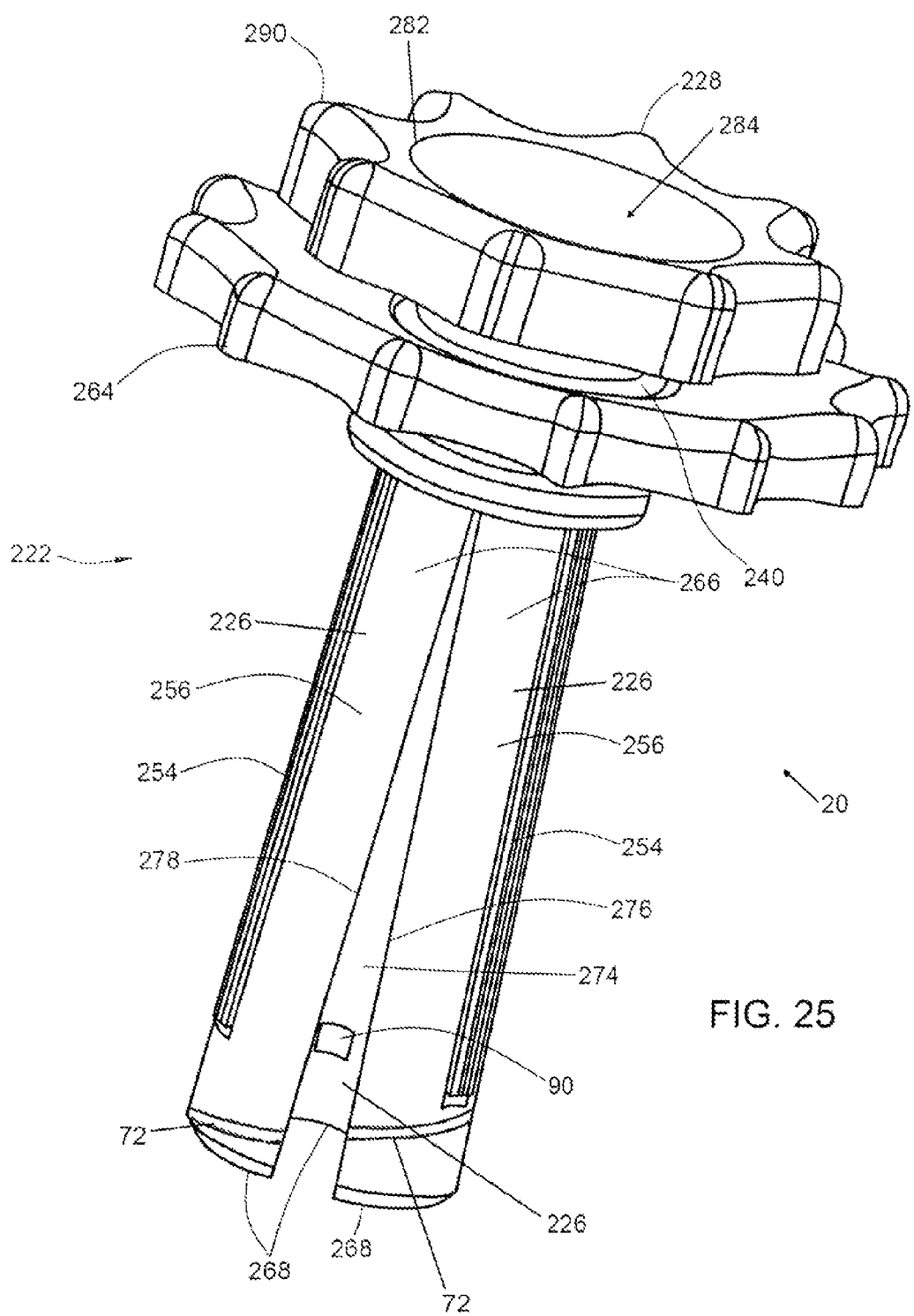
FIG. 25 is a perspective, bottom view of components of one embodiment of the embodiment shown in FIG. 13.

The same or similar thread configurations may also be present in cannula 222. In some embodiments, outer surfaces 256 of vertical members 226 of cannula 222 each comprise outer thread form 72, as shown in FIGS. 19A, 24 and 25. Outer thread forms 72 of vertical members 226 are configured to mate with tissue, for example, to fix cannula 222 relative to the anatomy of a patient. In some embodiments, outer thread forms 72 of vertical members 226 may have different pitches. In some embodiments, outer thread forms 72 of vertical members 226 are positioned below ridges 254 and may interrupt and/or extend across and/or through ridges 254.

Figure 34:
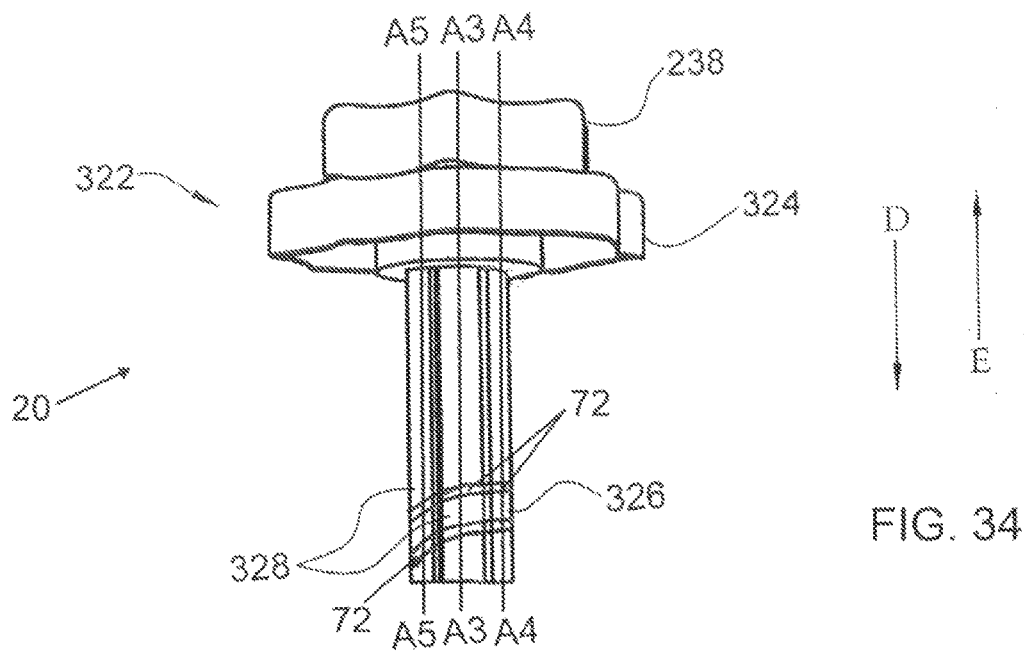
FIG. 34 is a side view of components of one embodiment of the embodiment shown in FIG. 26.
Figure 35:
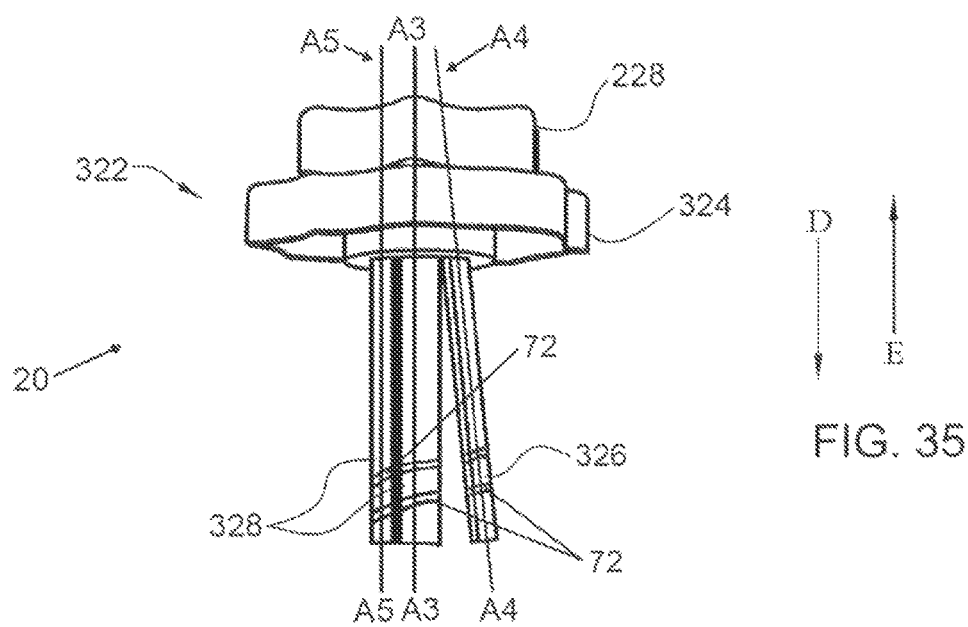
FIG. 35 is a side view of components of one embodiment of the embodiment shown in FIG. 26.

Similarly, thread configurations may also be present in cannula 322. The outer surface of at least one vertical member 326 and/or at least one vertical member 328 comprises outer thread form 72, as shown in FIGS. 34 and 35. As with cannulas 22, and 222, outer thread forms 72 of vertical members 326, 328 of cannula 322 are configured to mate with tissue so as to anchor or fix cannula 322 relative to the anatomy of a patient. In some embodiments, outer thread forms 72 of vertical members 326, 328 may have different pitches.

In assembly, operation and use, surgical system 20, described above, is employed, for example, with a minimally invasive surgical procedure for spinal and neurosurgical applications with a patient. For example, during spine surgery, a surgeon will make an incision in the skin of a patient's back over vertebrae to be treated. One or more dilators may be employed to gradually separate the muscles and create a portal through which the surgery may be performed.

The cannulas described herein help prevent dorsal movement of the cannulas by providing an anchor to prevent such unintended movement of the cannula. As stated above, this securing anchor is created by screwing cannula 22 into surrounding tissue at a suitable location within the patient's body. For instance, a sequential dilator system can be used to create an access opening to the spine. Cannula 22 can be secured by screwing it over the last sequential dilator, rotating it so that threads on the outer surface of cannula 22 grab the surrounding tissue and secure it in place. As cannula 22 faces dorsal forces, first vertical member 26 and second vertical member 28 are capable of expanding, thus further securing the cannula in place.

Once cannula 22 is in position, cannula 22 can be moved from the narrowed configuration to an expanded configuration by rotating top nut 24 relative to first vertical member 26 in a first direction such that top nut 24 moves in the direction shown by arrow C in FIG. 1A. Top nut 24 can be rotated in the first direction until planar end surface 52 of top nut 24 contacts flange 58 thereby causing lip 98 of second vertical member 28 to move relative to flange 58 of first vertical member 26 such that lower surface 107 of lip 98 of second vertical member 28 engages upper surface 59 of flange 58 of first vertical member 26, as shown in FIG. 5A. When lower surface 107 of lip 98 engages upper surface 59 of flange 58, longitudinal axis B extends transverse to longitudinal axis A, as shown in FIG. 5A and is in an expanded configuration. In some embodiments, as cannula 22 moves from the narrowed configuration to the expanded configuration, first vertical member 26 moves relative to second vertical member 28 such that protrusions 70 of second vertical member 28 move out of recesses 68 of first vertical member 26, as shown in FIG. 10.

When cannula 22 is in the expanded configuration, outer surfaces 71, 110 of first and second vertical members 26, 28 engage surrounding tissues, such as, for example, soft tissue, ligaments, tendons, cartilage and/or bone. First and second vertical members 26, 28 aid in spacing apart tissue and create access and/or a surgical pathway to a surgical site. That is, when cannula 22 in the expanded configuration, an item, such as, for example, a surgical instrument may be inserted through a pathway defined by passageway 66 of first vertical member 26 and conduit 116 of second vertical member 28 and/or a surgical procedure may be performed within the pathway.

Figure 22:
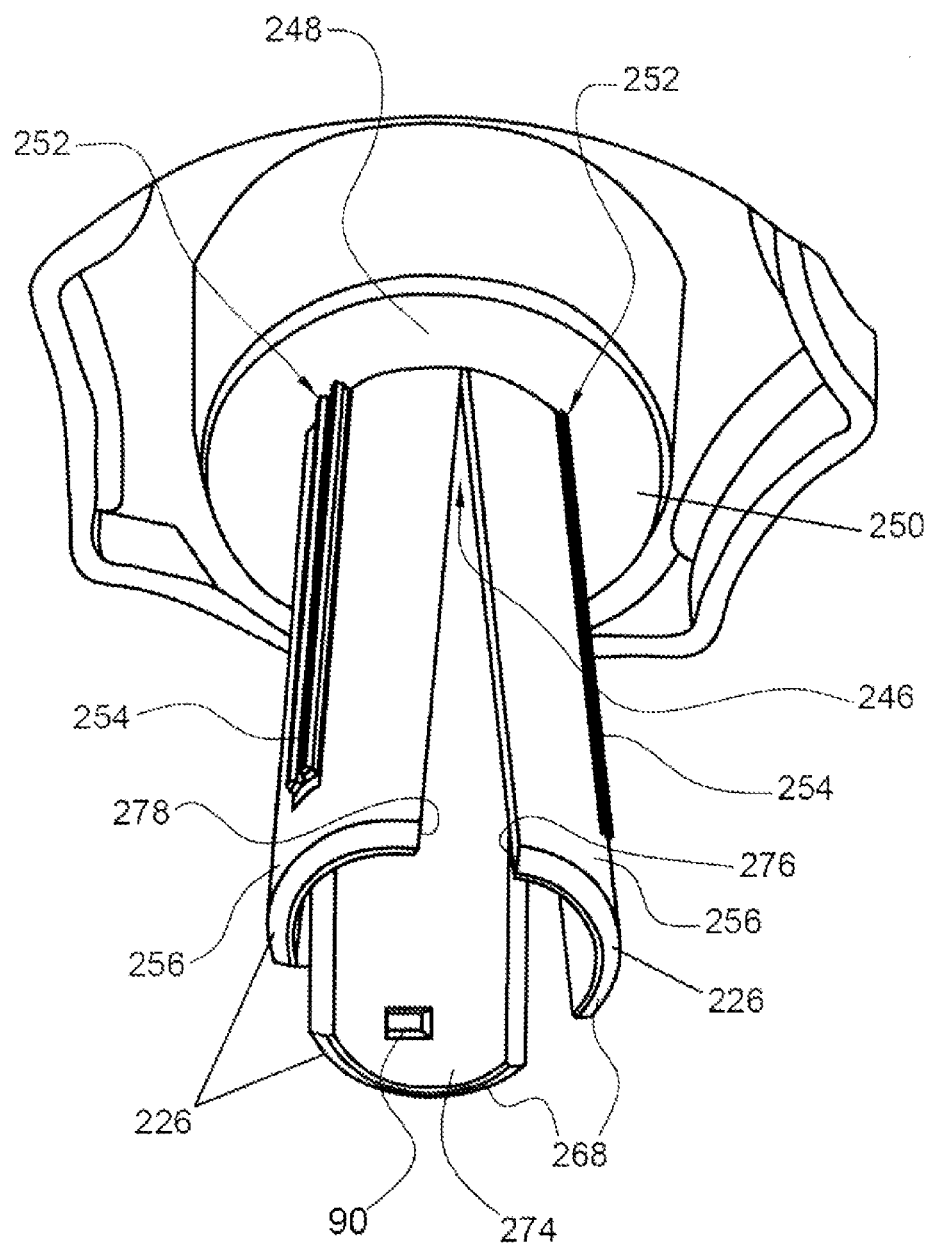
FIG. 22 is a perspective, bottom view of components of the embodiment shown in FIG. 13.

Cannula 222 is used in a similar manner as to that described above for cannula 22. Cannula 222 in the narrowed configuration discussed above and shown in FIGS. 16A and 17, for example, is passed through an incision in a patient to create a passageway or portal to the surgical site. Cannula 222 may then be rotated about axis A1 to translate cannula 222 within the patient's anatomy along axis A1 in the direction shown by arrow B in FIG. 17. Once cannula 222 is selectively positioned within the patient's anatomy, cannula 222 is moved from the narrowed configuration to the expanded configuration in the manner discussed above and shown in FIGS. 13, 21 and 22. When cannula 222 is in the expanded configuration, an axial surface 276 is spaced apart from an axial surface 278 at least at distal ends 268 of vertical members 226, as shown in FIGS. 13, 21 and 22. As with cannula 22, when cannula 222 is in the expanded configuration outer surfaces 256 of vertical members 226 engage surrounding tissue to create access and/or a surgical pathway to a surgical site.

Upon completion of the surgical procedure, top nut 228 is rotated relative to gripping portion 264 in a second direction, opposite the first direction, until end surface 292 of top nut 228 is spaced apart from top surfaces 294 of vertical members 226. This moves cannula 222 from the expanded configuration, shown in FIGS. 13, 21 and 22, to the narrowed configuration, shown in FIGS. 16A and 17. Once in the closed configuration, cannula 222 is removed from the surgical site.

Cannula 322 may be used in a same or similar manner as to that described above for cannulas 22 and 222. When cannula 322 is in the narrowed configuration, inner surfaces 372, 384 of vertical members 326, 328 define a conduit having a circular or polygonal cross sectional configuration, as shown in FIG. 32. Cannula 322 can be rotated about longitudinal axis A3 within the patient's anatomy such that thread forms 72 of vertical members 326, 328 engage surrounding tissue so as to anchor or thread the cannula into the surgical site. Cannula 322 may then be rotated about axis A3 to translate cannula 322 within the patient's anatomy along axis A3 in the direction shown by arrow D in FIG. 34. Once cannula 322 is selectively positioned within the patient's anatomy, cannula 322 is moved from the narrowed configuration, shown in FIG. 26, to the expanded configuration, shown in FIG. 27, in the manner discussed above. When cannula 322 is in the expanded configuration outer surfaces of vertical members 326, 328 engage surrounding tissue. Vertical members 326, 328 space apart tissue and create access and/or a surgical pathway to a surgical site and anchor the cannula in place. When cannula 322 is in the expanded configuration, an item, such as, for example, a surgical instrument may be inserted through lumen 284 of top nut 228 and passageway 334 of gripping portion 324 and into a conduit defined by inner surfaces 370, 384 of vertical members 326, 328.

Upon completion of the surgical procedure, top nut 228 is rotated relative to gripping portion 324 in a second direction opposite the first direction such that top nut 228 moves relative to gripping portion 324 in the direction shown by arrow E in FIGS. 26 and 27. Once cannula 322 is free to move, it can be removed from the surgical site.

As stated above, cannulas 22, 222 and 322 may be equipped with lights as described above. The lights can be used when the cannulas are in place so as to illuminate the surgical pathway to a surgical site. As discussed above the lights can be LED lights and are positioned so as to reduce shadowing making the illumination more affective for viewing during surgery.

It is envisioned that the use of microsurgical and image guided technologies may be employed to access, view and repair spinal deterioration or damage, with the aid of cannulas 22, 222 or 322. It is contemplated that a surgical procedure may employ other instruments that can be mounted with cannulas 22, 222 or 322, such as, for example, nerve root retractors, tissue retractors, forceps, cutter, drills, scrapers, reamers, rongeurs, taps, cauterization instruments, irrigation and/or aspiration instruments, illumination instruments, inserter instruments and/or separators, such as, for example, one or more burrs.

As stated above, cannulas 22, 222 and/or 322 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument, comprising:
   a handling portion comprising an inner surface defining a passageway that extends along a longitudinal axis, the handling portion comprising an annular flange that extends inwardly from the inner surface toward the passageway;
   a plurality of vertical members positioned within the passageway, proximal ends of the vertical members each comprising a lip having a proximal surface and an opposite distal surface that engages the flange; and
   a top nut that engages the handling portion, wherein the top nut is movable between a first configuration in which an end surface of the top nut is spaced apart from the lips and distal end portions of the vertical members each extend parallel to the longitudinal axis, and a second configuration in which the end surface engages the proximal surface of each of the lips and the distal end portions each extend at an acute angle relative to the longitudinal axis.

2. The surgical instrument recited in claim 1, wherein the top nut comprises external threading and the handling portion comprises internal threading that engages the external threading of the top nut to translate the top nut relative to the handling portion.

3. The surgical instrument recited in claim 1, wherein at least one of the vertical members comprises a light source configured to illuminate a surgical pathway.

4. The surgical instrument recited in claim 1, wherein the lips each extend at an acute angle relative to the distal end portion of a respective one of the vertical members.

5. The surgical instrument recited in claim 1, wherein the flange comprises a plurality of slots, the vertical members each including a ridge positioned in one of the slots.

6. The surgical instrument recited in claim 5, wherein the slots are disposed radially about the flange and are spaced apart from one another.

7. The surgical instrument recited in claim 5, wherein the slots are evenly spaced apart from one another.

8. The surgical instrument recited in claim 5, wherein an inner surface of the flange is continuously curved between adjacent ones of the slots.

9. The surgical instrument recited in claim 1, wherein the vertical members each comprise an inner surface that is concavely curved between axial end surfaces of the vertical members.

10. The surgical instrument recited in claim 1, wherein axial end surfaces of the vertical members each engage an axial end surface of an adjacent one of the vertical members when the top nut is in the first configuration.

11. The surgical instrument recited in claim 1, wherein inner surfaces of the vertical members define a working channel that is coaxial with the passageway, the working channel having a narrowed configuration when the top nut is in the first configuration and an expanded configuration when the top nut is in the second configuration.

12. The surgical instrument recited in claim 1, wherein the flange extends perpendicular to the longitudinal axis.

13. The surgical instrument recited in claim 1, wherein the instrument comprises three of the vertical members.

14. The surgical instrument recited in claim 1, wherein the vertical members each extend along a second longitudinal axis between the proximal end of a respective one of the vertical members and the distal end portion of the respective one of the vertical members, the second longitudinal axes being parallel to the longitudinal axis when the top nut is in the first configuration, the second longitudinal axes being at an acute angle relative to the longitudinal axis when the top nut is in the second configuration.

15. A method of using a surgical instrument, comprising:
providing a surgical instrument comprising:
   a handling portion comprising an inner surface defining a passageway that extends along a longitudinal axis, the handling portion comprising an annular flange that extends inwardly from the inner surface toward the passageway,
   a plurality of vertical members positioned within the passageway, proximal ends of the vertical members each comprising a lip having a proximal surface and an opposite distal surface that engages the flange, and
   a top nut that engages the handling portion; and
rotating the top nut such that an end surface of the top nut engages the proximal surface of each of the lips to move the vertical members from a first configuration in which distal end portions of the vertical members each extend parallel to the longitudinal axis to a second configuration in which the distal end portions each extend at an acute angle relative to the longitudinal axis.

16. The method recited in claim 15, wherein the top nut comprises external threading and the handling portion comprises internal threading, and the external threading engages the internal threading such that rotation of the top nut relative to the handling portion translates the top nut axially relative to the handling portion.

17. The method recited in claim 15 further comprising adjusting the position of the surgical instrument after rotating the top nut relative to the handling portion.

18. The method recited in claim 15, wherein at least one of the vertical members comprises a light source configured to illuminate a surgical pathway.

19. A surgical instrument, comprising:
   a first member comprising an inner surface defining a passageway defining a first longitudinal axis, the first member including an annular flange that extends inwardly from the inner surface toward the passageway, the flange extending perpendicular to the first longitudinal axis;
   a second member positioned in the passageway and comprising a lip having a proximal surface and an opposite distal surface that engages the flange, the lip extending at an acute angle relative to a second longitudinal axis defined by the second member; and
   a third member rotatably disposed in the passageway,
   wherein the third member is movable between a first configuration in which an end surface of the third member is spaced apart from the lip and the second member extends parallel to the first longitudinal axis and a second configuration in which the end surface engages the proximal surface and the second member extends at an acute angle relative to the first longitudinal axis.

20. The surgical instrument recited in claim 19, wherein:
the second member comprises a plurality of second members, the second members each comprising a pair of axial surfaces; and
the axial surfaces of a respective second member engages axial surfaces of adjacent second members when the second members are in the first configuration and are spaced apart from axial surfaces of adjacent second members when the second members are in the second configuration.

* * * * *